(12) United States Patent  
Fangrow, Jr.

(10) Patent No.: US 8,221,391 B2  
(45) Date of Patent: Jul. 17, 2012

(54) NEEDLELESS MEDICAL CONNECTOR

(75) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 12/844,791

(22) Filed: Jul. 27, 2010

(65) Prior Publication Data

US 2011/0022031 A1  Jan. 27, 2011

Related U.S. Application Data

(63) Continuation of application No. 11/417,925, filed on May 3, 2006, now Pat. No. 7,763,199, which is a continuation of application No. 11/157,216, filed on Jun. 20, 2005, now abandoned, which is a continuation of application No. 10/636,163, filed on Aug. 7, 2003, now Pat. No. 6,916,309, which is a continuation of application No. 09/614,001, filed on Jul. 11, 2000, now Pat. No. 6,695,817.

(51) Int. Cl.  
*A61M 39/02* (2006.01)

(52) U.S. Cl. ........................................ 604/539; 604/533

(58) Field of Classification Search .......... 604/174–180, 604/246–256, 96.01, 164.01, 523  
See application file for complete search history.

(56) References Cited

U.S. PATENT DOCUMENTS

| | | | |
|---|---|---|---|
| 1,578,517 A | 3/1926 | Hein | |
| 2,210,098 A | 8/1940 | Ravenscroft | |
| 2,289,677 A | 7/1942 | Perelson | |
| 2,756,282 A | 7/1956 | Deane | |
| 2,756,740 A | 7/1956 | Deane | |
| 2,847,995 A | 8/1958 | Adams | |
| 2,999,499 A | 9/1961 | Willet | |
| 3,134,380 A | 5/1964 | Armao | |

(Continued)

FOREIGN PATENT DOCUMENTS

CA  1105959  7/1981

(Continued)

OTHER PUBLICATIONS

ICU's Preliminary Invalidity Contentions related to U.S. Patent No. 5,730,418 C1, Case No. SA CV 06-619 MRP ANx, Jan. 8, 2007.

(Continued)

*Primary Examiner* — Kevin C Sirmons  
*Assistant Examiner* — Phillip Gray  
(74) *Attorney, Agent, or Firm* — Knobbe, Martens, Olson & Bear, LLP

(57) ABSTRACT

A valve for selectively permitting a fluid flow between first and second medical implements is disclosed. The valve has a housing with an interface suitable for receiving a connector portion of a first medical device such as a catheter, and a seal made of a flexible material. The seal has a first end in fluid communication with the interface, a second end suitable for receiving the second medical device, and at least one slit in fluid communication with the first end and the second end. The slit defines a restricted fluid flow path and a relatively small interior volume when in an undisturbed state, defines an expanded fluid flow path and a larger interior volume upon the introduction of the second medical instrument into the slit, and retracts to define a restricted flow path and a small interior volume upon the withdrawal of the second medical device from the seal.

11 Claims, 19 Drawing Sheets

U.S. PATENT DOCUMENTS

| | | |
|---|---|---|
| 3,135,261 A | 6/1964 | Carroll |
| 3,171,412 A | 3/1965 | Willet |
| 3,191,655 A | 6/1965 | McCord |
| 3,193,154 A | 7/1965 | Bross |
| 3,334,860 A | 8/1967 | Bolton, Jr. |
| 3,352,531 A | 11/1967 | Kilmarx |
| 3,354,881 A | 11/1967 | Bloch |
| 3,385,301 A | 5/1968 | Harautuneian |
| 3,502,097 A | 3/1970 | Muller |
| 3,570,484 A | 3/1971 | Steer et al. |
| 3,630,199 A | 12/1971 | Gangarosa |
| 3,648,684 A | 3/1972 | Barnwell et al. |
| 3,659,602 A | 5/1972 | Cloyd |
| 3,726,282 A | 4/1973 | Patel |
| 3,788,519 A | 1/1974 | Mengel |
| 3,831,629 A | 8/1974 | Mackal et al. |
| 3,852,385 A | 12/1974 | Huggins |
| 3,861,388 A | 1/1975 | Vaughn |
| 3,896,853 A | 7/1975 | Bernhard |
| 3,965,910 A | 6/1976 | Fischer |
| 3,974,832 A | 8/1976 | Kruck |
| 3,976,063 A | 8/1976 | Henneman et al. |
| 3,976,073 A | 8/1976 | Quick et al. |
| 3,977,403 A | 8/1976 | Patel |
| 3,986,508 A | 10/1976 | Barrington |
| 3,993,063 A | 11/1976 | Larrabee |
| 3,994,293 A | 11/1976 | Ferro |
| 4,005,710 A | 2/1977 | Zeddies et al. |
| 4,019,512 A | 4/1977 | Tenczar |
| 4,022,205 A | 5/1977 | Tenczar |
| 4,040,420 A | 8/1977 | Speer |
| 4,076,285 A | 2/1978 | Martinez |
| 4,079,738 A | 3/1978 | Dunn et al. |
| 4,080,965 A | 3/1978 | Phillips |
| 4,121,585 A | 10/1978 | Becker, Jr. |
| 4,128,098 A | 12/1978 | Bloom et al. |
| 4,133,441 A | 1/1979 | Mittleman et al. |
| 4,143,853 A | 3/1979 | Abramson |
| 4,149,535 A | 4/1979 | Volder |
| 4,161,949 A | 7/1979 | Thanawalla |
| 4,187,846 A | 2/1980 | Lolachi et al. |
| 4,191,183 A | 3/1980 | Mendelson |
| 4,214,779 A | 7/1980 | Losell |
| 4,219,912 A | 9/1980 | Adams |
| 4,243,034 A | 1/1981 | Brandt |
| 4,257,416 A | 3/1981 | Prager |
| 4,294,249 A | 10/1981 | Sheehan et al. |
| 4,296,949 A | 10/1981 | Muetterties et al. |
| 4,306,705 A | 12/1981 | Svensson |
| 4,324,239 A | 4/1982 | Gordon et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,346,703 A | 8/1982 | Dennehey et al. |
| 4,362,156 A | 12/1982 | Feller, Jr. et al. |
| 4,387,879 A | 6/1983 | Tauschinski |
| 4,392,851 A | 7/1983 | Elias |
| 4,405,163 A | 9/1983 | Voges et al. |
| 4,405,312 A | 9/1983 | Gross et al. |
| 4,411,662 A | 10/1983 | Pearson |
| 4,417,890 A | 11/1983 | Dennehey et al. |
| 4,421,296 A | 12/1983 | Stephens |
| 4,432,759 A | 2/1984 | Gross et al. |
| 4,432,765 A | 2/1984 | Oscarsson |
| 4,439,188 A | 3/1984 | Dennehey et al. |
| 4,439,193 A | 3/1984 | Larkin |
| 4,449,693 A | 5/1984 | Gereg |
| 4,457,749 A | 7/1984 | Bellotti et al. |
| 4,483,368 A | 11/1984 | Panthofer |
| 4,508,367 A | 4/1985 | Oreopoulos et al. |
| 4,511,359 A | 4/1985 | Vaillancourt |
| 4,512,766 A | 4/1985 | Vailancourt |
| 4,564,054 A | 1/1986 | Gustavsson |
| 4,592,356 A | 6/1986 | Gutierrez |
| 4,607,868 A | 8/1986 | Harvey et al. |
| 4,610,469 A | 9/1986 | Wolff-Mooij |
| 4,617,012 A | 10/1986 | Vaillancourt |
| 4,619,640 A | 10/1986 | Poholshy et al. |
| 4,623,068 A | 11/1986 | Brown et al. |
| 4,645,494 A | 2/1987 | Lee et al. |
| 4,666,429 A | 5/1987 | Stone |
| 4,673,400 A | 6/1987 | Martin |
| 4,706,487 A | 11/1987 | Bandou et al. |
| 4,710,168 A | 12/1987 | Schwab et al. |
| 4,725,267 A | 2/1988 | Vaillancourt |
| 4,752,292 A | 6/1988 | Lopez et al. |
| 4,759,756 A | 7/1988 | Forman et al. |
| 4,775,369 A | 10/1988 | Schwartz |
| 4,778,447 A | 10/1988 | Velde et al. |
| 4,778,453 A | 10/1988 | Lopez |
| 4,781,702 A | 11/1988 | Herrli |
| 4,804,015 A | 2/1989 | Albinsson |
| 4,810,241 A | 3/1989 | Rogers |
| 4,813,938 A | 3/1989 | Raulerson |
| 4,819,684 A | 4/1989 | Zaugg et al. |
| 4,832,214 A | 5/1989 | Schrader et al. |
| 4,834,664 A | 5/1989 | Lin |
| 4,834,716 A | 5/1989 | Ogle, II |
| 4,874,377 A | 10/1989 | Newgard et al. |
| 4,878,897 A | 11/1989 | Katzin |
| 4,880,414 A | 11/1989 | Whipple |
| 4,889,527 A | 12/1989 | Herrli |
| 4,915,687 A | 4/1990 | Sivert |
| 4,917,668 A | 4/1990 | Haindl |
| 4,928,212 A | 5/1990 | Benavides |
| 4,943,896 A | 7/1990 | Johnson |
| 4,946,445 A | 8/1990 | Lynn |
| 4,963,133 A | 10/1990 | Whipple |
| 4,964,855 A | 10/1990 | Todd et al. |
| 4,969,883 A | 11/1990 | Gilbert et al. |
| 4,991,413 A | 2/1991 | Arnaldo |
| 4,991,629 A | 2/1991 | Ernesto et al. |
| 4,998,713 A | 3/1991 | Vaillancourt |
| 4,998,927 A | 3/1991 | Vaillancourt |
| 5,006,114 A | 4/1991 | Rogerts et al. |
| 5,009,490 A | 4/1991 | Kouno et al. |
| 5,018,532 A | 5/1991 | Ethridge, III |
| 5,024,657 A | 6/1991 | Needham et al. |
| 5,031,675 A | 7/1991 | Lindgren |
| 5,041,087 A | 8/1991 | Loo et al. |
| 5,046,456 A | 9/1991 | Heyman et al. |
| 5,049,128 A | 9/1991 | Duquette |
| D321,250 S | 10/1991 | Jepson et al. |
| D321,251 S | 10/1991 | Jepson et al. |
| 5,061,253 A | 10/1991 | Yoshida |
| 5,064,416 A | 11/1991 | Newgard |
| 5,065,783 A | 11/1991 | Ogle, II |
| 5,100,394 A | 3/1992 | Dudar et al. |
| 5,114,408 A | 5/1992 | Fleischhaker et al. |
| 5,122,123 A | 6/1992 | Vaillancourt |
| 5,125,915 A | 6/1992 | Berry et al. |
| 5,135,489 A | 8/1992 | Jepson et al. |
| 5,137,524 A | 8/1992 | Lynn et al. |
| 5,147,333 A | 9/1992 | Raines |
| 5,154,703 A | 10/1992 | Bonaldo |
| 5,158,554 A | 10/1992 | Jepson et al. |
| 5,163,922 A | 11/1992 | McElveen et al. |
| 5,171,234 A | 12/1992 | Jepson et al. |
| 5,188,620 A | 2/1993 | Jepson et al. |
| 5,199,947 A | 4/1993 | Lopez et al. |
| 5,201,717 A | 4/1993 | Wyatt et al. |
| 5,203,775 A | 4/1993 | Frank et al. |
| 5,211,638 A | 5/1993 | Dudar et al. |
| 5,215,538 A | 6/1993 | Larkin |
| 5,221,271 A | 6/1993 | Nicholson et al. |
| 5,224,515 A | 7/1993 | Foster et al. |
| 5,242,393 A | 9/1993 | Brimhall et al. |
| 5,242,423 A | 9/1993 | Goodsir et al. |
| 5,242,425 A | 9/1993 | Whine et al. |
| 5,242,432 A | 9/1993 | DeFrank |
| 5,251,873 A | 10/1993 | Atkinson et al. |
| 5,253,842 A | 10/1993 | Huebscher et al. |
| 5,255,676 A | 10/1993 | Russo |
| 5,256,155 A | 10/1993 | Yerlikaya et al. |
| 5,267,966 A | 12/1993 | Paul |
| 5,269,771 A | 12/1993 | Thomas et al. |

| | | | | | | |
|---|---|---|---|---|---|---|
| 5,273,533 A | 12/1993 | Bonaldo | | 5,901,942 A | 5/1999 | Lopez |
| 5,280,876 A | 1/1994 | Atkins | | 5,928,204 A | 7/1999 | Lopez |
| 5,284,475 A | 2/1994 | Mackal | | 5,935,620 A | 8/1999 | Baudin |
| 5,290,254 A | 3/1994 | Vaillancourt | | 5,947,954 A | 9/1999 | Bonaldo |
| 5,293,902 A | 3/1994 | Lapierie | | 5,957,898 A | 9/1999 | Jepson et al. |
| 5,295,657 A | 3/1994 | Atkinson | | 5,967,490 A | 10/1999 | Pike |
| 5,306,265 A | 4/1994 | Ragazzi | | 5,979,868 A | 11/1999 | Wu et al. |
| 5,312,083 A | 5/1994 | Ekman | | 6,009,902 A | 1/2000 | Troiani et al. |
| 5,312,377 A | 5/1994 | Dalhon | | 6,019,748 A | 2/2000 | Lopez |
| 5,322,518 A | 6/1994 | Schneider | | 6,029,946 A | 2/2000 | Doyle |
| 5,324,270 A | 6/1994 | Kayan et al. | | 6,036,171 A | 3/2000 | Weinheimer et al. |
| 5,342,316 A | 8/1994 | Wallace | | 6,048,335 A | 4/2000 | Mayer |
| 5,342,326 A | 8/1994 | Peppel et al. | | 6,050,978 A | 4/2000 | Orr et al. |
| 5,344,414 A | 9/1994 | Lopez et al. | | 6,063,062 A | 5/2000 | Paradis |
| 5,348,542 A | 9/1994 | Ellis | | 6,079,432 A | 6/2000 | Paradis |
| 5,353,837 A | 10/1994 | Faust | | 6,089,541 A | 7/2000 | Weinheimer et al. |
| 5,360,413 A | 11/1994 | Leason et al. | | 6,113,068 A | 9/2000 | Ryan |
| 5,380,306 A | 1/1995 | Brinon | | 6,117,114 A | 9/2000 | Paradis |
| 5,389,086 A | 2/1995 | Attermeier et al. | | 6,132,403 A | 10/2000 | Lopez |
| 5,398,530 A | 3/1995 | Derman | | 6,132,404 A | 10/2000 | Lopez |
| 5,401,245 A | 3/1995 | Haining | | 6,142,446 A | 11/2000 | Leinsing |
| 5,407,437 A | 4/1995 | Heimreid | | 6,152,900 A | 11/2000 | Mayer |
| 5,411,483 A | 5/1995 | Loomas et al. | | 6,162,251 A | 12/2000 | Kredovski |
| 5,411,499 A | 5/1995 | Dudar et al. | | 6,170,800 B1 | 1/2001 | Meloul et al. |
| 5,417,673 A | 5/1995 | Gordon | | 6,171,287 B1 | 1/2001 | Lynn et al. |
| 5,439,451 A | 8/1995 | Collinson et al. | | 6,206,861 B1 | 3/2001 | Mayer |
| 5,439,452 A | 8/1995 | McCarty | | 6,245,048 B1 | 6/2001 | Fangrow et al. |
| 5,442,941 A | 8/1995 | Kahonen et al. | | 6,254,579 B1 | 7/2001 | Cogger et al. |
| 5,456,676 A | 10/1995 | Nelson et al. | | 6,261,282 B1 | 7/2001 | Jepson et al. |
| 5,470,319 A | 11/1995 | Mayer | | 6,299,132 B1 | 10/2001 | Weinheimer et al. |
| 5,474,544 A | 12/1995 | Lynn | | 6,325,782 B1 | 12/2001 | Lopez |
| 5,480,393 A | 1/1996 | Bommarito | | 6,364,869 B1 | 4/2002 | Bonaldo |
| 5,487,731 A | 1/1996 | Denton | | 6,428,520 B1 | 8/2002 | Lopez et al. |
| 5,501,426 A * | 3/1996 | Atkinson et al. ............ 251/149.1 | | 6,543,745 B1 | 4/2003 | Enerson |
| 5,509,433 A | 4/1996 | Paradis | | 6,572,592 B1 | 6/2003 | Lopez |
| 5,520,665 A | 5/1996 | Fleetwood | | 6,599,273 B1 | 7/2003 | Lopez |
| 5,533,708 A | 7/1996 | Atkinson et al. | | 6,609,696 B2 | 8/2003 | Enerson |
| 5,533,996 A | 7/1996 | Murphey et al. | | 6,635,044 B2 | 10/2003 | Lopez |
| 5,535,771 A | 7/1996 | Purdy et al. | | 6,651,956 B2 | 11/2003 | Miller |
| 5,535,785 A | 7/1996 | Werge et al. | | 6,669,673 B2 | 12/2003 | Lopez |
| 5,540,661 A | 7/1996 | Tomisaka et al. | | 6,682,509 B2 | 1/2004 | Lopez |
| 5,549,566 A | 8/1996 | Elias et al. | | 6,695,817 B1 | 2/2004 | Fangrow |
| 5,549,577 A | 8/1996 | Siegel et al. | | 6,706,022 B1 | 3/2004 | Leinsing et al. |
| 5,549,651 A | 8/1996 | Lynn | | 6,712,791 B2 | 3/2004 | Lui et al. |
| 5,555,908 A | 9/1996 | Edwards et al. | | 6,758,833 B2 | 7/2004 | Lopez |
| 5,556,388 A | 9/1996 | Johlin, Jr. | | 6,840,501 B2 | 1/2005 | Doyle |
| 5,569,235 A | 10/1996 | Ross et al. | | 6,866,656 B2 | 3/2005 | Tingey et al. |
| 5,573,516 A | 11/1996 | Tyner | | 6,871,838 B2 | 3/2005 | Raines et al. |
| 5,577,706 A | 11/1996 | King | | 6,908,459 B2 | 6/2005 | Harding et al. |
| 5,578,059 A | 11/1996 | Patzer | | 6,916,309 B2 | 7/2005 | Fangrow |
| 5,597,536 A | 1/1997 | Mayer | | 6,932,795 B2 | 8/2005 | Lopez et al. |
| 5,603,706 A | 2/1997 | Wyatt et al. | | 7,014,169 B2 | 3/2006 | Newton et al. |
| 5,609,584 A | 3/1997 | Gettig et al. | | 7,025,744 B2 | 4/2006 | Utterberg et al. |
| 5,616,129 A | 4/1997 | Mayer | | 7,074,216 B2 | 7/2006 | Fowles et al. |
| 5,616,130 A | 4/1997 | Mayer | | 7,100,890 B2 | 9/2006 | Cote et al. |
| 5,620,424 A | 4/1997 | Abramson | | 7,306,197 B2 | 12/2007 | Parrino et al. |
| 5,620,434 A | 4/1997 | Brony | | 7,497,849 B2 | 3/2009 | Fangrow |
| 5,674,206 A | 10/1997 | Allton et al. | | 7,628,774 B2 | 12/2009 | Fangrow |
| 5,676,346 A | 10/1997 | Leinsing | | 7,763,199 B2 | 7/2010 | Fangrow |
| 5,685,866 A | 11/1997 | Lopez | | 7,824,393 B2 | 11/2010 | Fangrow |
| 5,690,612 A | 11/1997 | Lopez et al. | | 2001/0049508 A1 | 12/2001 | Fangrow et al. |
| 5,694,686 A | 12/1997 | Lopez | | 2002/0082586 A1 | 6/2002 | Finley et al. |
| 5,695,466 A | 12/1997 | Lopez et al. | | 2002/0147431 A1 | 10/2002 | Lopez et al. |
| 5,699,821 A | 12/1997 | Paradis | | 2003/0036735 A1 | 2/2003 | Jepson et al. |
| 5,700,248 A | 12/1997 | Lopez | | 2003/0050610 A1 | 3/2003 | Newton et al. |
| 5,730,418 A | 3/1998 | Feith et al. | | 2003/0098430 A1 | 5/2003 | Leinsing et al. |
| 5,738,663 A | 4/1998 | Lopez | | 2003/0141477 A1 | 7/2003 | Miller |
| 5,749,861 A | 5/1998 | Guala et al. | | 2003/0209681 A1 | 11/2003 | Leinsing et al. |
| 5,782,816 A | 7/1998 | Werschmidt et al. | | 2004/0006330 A1 | 1/2004 | Fangrow |
| 5,797,897 A | 8/1998 | Jepson et al. | | 2004/0030321 A1 | 2/2004 | Fangrow |
| 5,806,551 A | 9/1998 | Meloul et al. | | 2004/0199126 A1 | 10/2004 | Harding et al. |
| 5,806,831 A | 9/1998 | Paradis | | 2005/0038397 A1 | 2/2005 | Newton et al. |
| 5,820,601 A | 10/1998 | Mayer | | 2005/0212292 A1 | 9/2005 | Parrino et al. |
| 5,836,923 A | 11/1998 | Mayer | | 2005/0222541 A1 | 10/2005 | Lopez et al. |
| 5,839,715 A | 11/1998 | Leinsing | | 2006/0004331 A1 | 1/2006 | Fangrow |
| 5,843,046 A | 12/1998 | Motisi et al. | | 2006/0161115 A1 | 7/2006 | Fangrow |
| 5,865,807 A | 2/1999 | Blake, III | | 2006/0200088 A1 | 9/2006 | Lopez et al. |
| 5,873,862 A | 2/1999 | Lopez | | 2006/0200089 A1 | 9/2006 | Lopez et al. |
| 5,882,348 A | 3/1999 | Winterton et al. | | 2006/0200090 A1 | 9/2006 | Lopez et al. |

| | | | |
|---|---|---|---|
| 2006/0206061 | A1 | 9/2006 | Lopez et al. |
| 2006/0211997 | A1 | 9/2006 | Fangrow |
| 2006/0211998 | A1 | 9/2006 | Fangrow |
| 2006/0211999 | A1 | 9/2006 | Fangrow |
| 2006/0212000 | A1 | 9/2006 | Fangrow |
| 2006/0212001 | A1 | 9/2006 | Fangrow |
| 2006/0212002 | A1 | 9/2006 | Fangrow |
| 2006/0212003 | A1 | 9/2006 | Fangrow |
| 2006/0212006 | A1 | 9/2006 | Fangrow |
| 2006/0224127 | A1 | 10/2006 | Fangrow |
| 2006/0264842 | A1 | 11/2006 | Fangrow |
| 2006/0264843 | A1 | 11/2006 | Fangrow |
| 2006/0264844 | A1 | 11/2006 | Fangrow |
| 2006/0264848 | A1 | 11/2006 | Fangrow |
| 2006/0264849 | A1 | 11/2006 | Lopez et al. |
| 2006/0264909 | A1 | 11/2006 | Fangrow |
| 2006/0264910 | A1 | 11/2006 | Fangrow |
| 2006/0270999 | A1 | 11/2006 | Fangrow |
| 2006/0271016 | A1 | 11/2006 | Fangrow |
| 2006/0276757 | A1 | 12/2006 | Fangrow |
| 2006/0276758 | A1 | 12/2006 | Fangrow |
| 2007/0112312 | A1 | 5/2007 | Fangrow |
| 2007/0112313 | A1 | 5/2007 | Fangrow |
| 2007/0175485 | A1 | 8/2007 | Funamura et al. |
| 2007/0224865 | A1 | 9/2007 | Fangrow |
| 2007/0233046 | A1 | 10/2007 | Funamura et al. |
| 2008/0086097 | A1 | 4/2008 | Rasmussen et al. |
| 2008/0086099 | A1 | 4/2008 | McKinnon et al. |
| 2008/0093571 | A1 | 4/2008 | Desecki |
| 2008/0103482 | A1 | 5/2008 | Fangrow |
| 2011/0046572 | A1 | 2/2011 | Fangrow |

FOREIGN PATENT DOCUMENTS

| | | |
|---|---|---|
| CA | 2149725 | 11/1995 |
| CA | 2175021 | 11/1996 |
| CH | 636526 | 6/1983 |
| CH | 670955 A5 | 7/1989 |
| DE | 855 319 | 9/1952 |
| DE | 84 25 197.2 | 10/1985 |
| DE | 37 40 269 A1 | 6/1989 |
| EP | 0 114 677 | 8/1984 |
| EP | 0 237 321 | 3/1987 |
| EP | 0 240 590 | 4/1987 |
| EP | 0 309 771 | 3/1988 |
| EP | 0 263 789 | 4/1988 |
| EP | 0 399 119 | 7/1989 |
| EP | 0 367 549 | 10/1989 |
| EP | 0 438 909 | 12/1990 |
| EP | 0 446 463 | 12/1990 |
| EP | 1 459 784 | 9/2004 |
| EP | 1 685 872 | 8/2006 |
| EP | 1 990 070 A2 | 11/2008 |
| EP | 1 990 070 A3 | 2/2009 |
| EP | 2 161 051 A1 | 3/2010 |
| FR | 2 439 022 | 5/1980 |
| GB | 2 019 219 A | 4/1979 |
| GB | 2 019 219 B | 10/1979 |
| GB | 2 034 185 A | 6/1980 |
| HU | P9902031 | 10/1999 |
| HU | P9902203 | 10/1999 |
| JP | 1 435 244 | 4/1988 |
| KR | 87-3257 | 4/1990 |
| NO | 310805 | 9/2001 |
| RU | 2 154 462 C2 | 6/1995 |
| WO | WO 86/01712 | 3/1986 |
| WO | WO 86/03416 | 6/1986 |
| WO | WO 93/11828 | 6/1993 |
| WO | WO 97/21463 | 6/1997 |
| WO | WO 97/21464 | 6/1997 |
| WO | WO 97/31676 A2 | 9/1997 |
| WO | WO 98/26835 | 6/1998 |
| WO | WO 99/58186 | 11/1999 |
| WO | WO 99/59672 | 11/1999 |
| WO | WO 99/61093 | 12/1999 |
| WO | WO 02/04065 A2 | 1/2002 |
| WO | WO 02/04065 A3 | 8/2002 |
| WO | WO 03/018104 | 3/2003 |
| WO | WO 03/086528 | 10/2003 |
| WO | WO 2005/011799 | 2/2005 |
| WO | WO 2005/115521 | 12/2005 |
| WO | WO 2006/013433 | 2/2006 |
| WO | WO 2006/052655 A2 | 5/2006 |
| WO | WO 2006/052655 A3 | 5/2006 |
| WO | WO 2007/098147 A3 | 8/2007 |

OTHER PUBLICATIONS

Order Granting Defendant ICU's Motion for Summary Judgment of Noninfringement, Filed in Case No. SA CV 06-619 MRP ANx, Sep. 14, 2007.

Expert Report of Paul DiPerna regarding Inequitable Conduct and Invalidity, Filed in Case No. SA CV 06-619 MRP ANx, Sep. 17, 2007.

Saechtling Tworzywa Sztuczne, WN-T Warszawa, 1999, vol. V Edition, pp. 224-225.

Reexamination proceedings U.S. Patent No. 5,730,418 (Reexamination Control No. 90/006,117) including the amendments filed by the owner of the patent during Reexamination proceedings, including the amendments received by the U.S. Patent & Trademark Office on Mar. 19, 2003 and Apr. 7, 2005.

U.S. Appl. No. 08/767,587, filed Dec. 16, 1996, including its prosecution history, including office communications dated Jul. 16, 1998 and Apr. 12, 1999.

U.S. Appl. No. 09/078,941, filed May 14, 1998, including its prosecution history, including office communications dated May 20, 1999, Sep. 15, 1999, May 31, 2000, Dec. 8, 2000, and May 2, 2001.

U.S. Appl. No. 09/411,988, filed Oct. 4, 1999, including its prosecution history, including office communications dated Jun. 13, 2000, Dec. 20, 2000, May 25, 2001, Dec. 4, 2001, and Apr. 30, 2002.

U.S. Appl. No. 09/614,011, filed Jul. 11, 2000, including its prosecution history, including office communications dated May 14, 2002, Sep. 11, 2002, and Apr. 4, 2003.

U.S. Appl. No. 09/879,364, filed Jun. 12, 2001, published as US 2001/0049508 on Dec. 6, 2001, including its prosecution history, including office communications dated Feb. 4, 2003, Dec. 16, 2003, Sep. 15, 2004, Jan. 7, 2005, Oct. 15, 2005, Feb. 1, 2006, Jun. 12, 2006, and Feb. 8, 2007.

U.S. Appl. No. 10/163,719, filed Jun. 5, 2002, published as US 2002/0147431 on Oct. 10, 2002, including its prosecution history, including office communications dated Dec. 23, 2003, Apr. 22, 2004, and Feb. 9, 2005.

U.S. Appl. No. 10/217,213, filed Dec. 16, 1996, including its prosecution history, including office communications dated Dec. 16, 2003, May 5, 2005, and Apr. 27, 2006.

U.S. Appl. No. 10/332,732, filed Jun. 2, 2003, published as US 2004/0006330 on Jan. 8, 2004, including its prosecution history, including office communications dated Jun. 15, 2006, Mar. 12, 2007, and Nov. 29, 2007.

U.S. Appl. No. 10/636,163, filed on Aug. 7, 2003, published as US 2004/0030321 on Feb. 12, 2004, including its prosecution history, including office communications dated Aug. 23, 2004 and Mar. 7, 2005.

U.S. Appl. No. 11/085,808, filed Mar. 21, 2005, published as US 2005/0222541 on Oct. 6, 2005, including its prosecution history, including office communications dated Nov. 3, 2008.

U.S. Appl. No. 11/157,216, filed Jun. 20, 2005, published as US 2006/0004331 on Jan. 5, 2006, including its prosecution history, including office communications dated Dec. 13, 2005, Sep. 7, 2006, and Apr. 7, 2008.

U.S. Appl. No. 11/267,822, filed May 3, 2006, published as US 2006/0161115 on Jul. 20, 2006, including its prosecution history, including office communications dated Dec. 12, 2006, Apr. 23, 2007, and Dec. 17, 2007.

U.S. Appl. No. 11/416,781, filed May 2, 2006, published as US 2006/0264842 on Nov. 23, 2006, including its prosecution history, including office communications dated Aug. 10, 2007 and Jul. 29, 2008.

U.S. Appl. No. 11/416,880, filed May 2, 2006, published as US 2006/0212000 on Sep. 21, 2006, including its prosecution history, including office communications dated Aug. 25, 2006, Feb. 23, 2007, Jun. 13, 2008, Apr. 7, 2009, and Sep. 22, 2009.

U.S. Appl. No. 11/416,930, filed May 2, 2006, published as US 2006/0224127 on Oct. 5, 2006, including its prosecution history, including office communications dated Jul. 30, 2007 and May 7, 2008.

U.S. Appl. No. 11/416,931, filed May 2, 2006, published as US 2006/0212001 on Sep. 21, 2006, including its prosecution history, including office communications dated Sep. 20, 2006 and Apr. 21, 2008.

U.S. Appl. No. 11/416,932, filed May 2, 2006, published as US 2006/0212002 on Sep. 21, 2006, including its prosecution history, including office communications dated Oct. 17, 2006, May 21, 2007, Sep. 25, 2007, Apr. 4, 2008, and Oct. 9, 2008.

U.S. Appl. No. 11/416,933, filed May 2, 2006, published as US 2006/0212003 on Sep. 21, 2006, including its prosecution history, including office communications dated Sep. 7, 2007 and Apr. 21, 2008.

U.S. Appl. No. 11/417,432, filed May 17, 2007, published as US 2007/0112312 on May 17, 2007, including its prosecution history, including office communications Jul. 31, 2006, Apr. 23, 2007, and Dec. 17, 2007.

U.S. Appl. No. 11/417,446, filed May 3, 2006, published as US 2006/0211997 on Sep. 21, 2006, including its prosecution history, including office communications dated Jul. 31, 2006, Apr. 23, 2007, and Dec. 14, 2007.

U.S. Appl. No. 11/417,472, filed May 3, 2006, published as US 2007/0112313 on May 17, 2007, including office communications dated Jul. 13, 2006, Apr. 23, 2007, and Dec. 14, 2007.

U.S. Appl. No. 11/417,486, filed May 3, 2006, published as US 2006/0270999 on Nov. 30, 2006, including its prosecution history, including office communications dated Apr. 24, 2007 and Apr. 18, 2008.

U.S. Appl. No. 11/417,527, filed May 3, 2006, published as US 2006/0276757 on Dec. 7, 2006, including its prosecution history, including office communications dated Dec. 14, 2006 and Dec. 13, 2007.

U.S. Appl. No. 11/417,675, filed May 3, 2006, published as US 2006/0264848 on Nov. 23, 2006, including its prosecution history, including office communications dated Apr. 20, 2007, Apr. 21, 2008, Dec. 22, 2008, Nov. 23, 2009, Feb. 23, 2010, and Jun. 14, 2010.

U.S. Appl. No. 11/417,771, filed May 3, 2006, published as US 2006/0200088 on Sep. 7, 2006, including its prosecution history, including office communications dated Sep. 30, 2008.

U.S. Appl. No. 11/417,773, filed May 3, 2006, published as US 2006/0200089 on Sep. 7, 2006, including its prosecution history.

U.S. Appl. No. 11/417,825, filed May 3, 2006, published as US 2006/0200090 on Sep. 7, 2006, including its prosecution history, including office communications dated Mar. 22, 2007, Jan. 28, 2008, Nov. 4, 2008, and Jul. 20, 2009.

U.S. Appl. No. 11/417,831, filed May 2, 2006, published as US 2006/0211998 on Sep. 21, 2006, including its prosecution history, including office communications dated Jul. 24, 2006, Apr. 20, 2007, and Dec. 14, 2007.

U.S. Appl. No. 11/417,843, filed May 3, 2006, published as US 2006/0264849 on Nov. 23, 2006, including its prosecution history, including office communications dated Feb. 8, 2008 and Sep. 29, 2008.

U.S. Appl. No. 11/417,853, filed May 3, 2006, published as US 2006/0212006 on Sep. 21, 2006, including its prosecution history, including office communications dated Oct. 13, 2006, Jun. 27, 2007, Mar. 19, 2008, Jul. 31, 2009, and Mar. 12, 2010.

U.S. Appl. No. 11/417,907, filed May 3, 2006, published as US 2006/0264909 on Nov. 23, 2006, including its prosecution history, including office communications dated Apr. 24, 3007 and Apr. 18, 2008.

U.S. Appl. No. 11/417,925, filed May 3, 2006, published as US 2006/0264843 on Nov. 23, 2006, including its prosecution history, including office communications dated Oct. 14, 2008, Jul. 14, 2009, Dec. 17, 2009, and Mar. 1, 2010.

U.S. Appl. No. 11/417,928, filed May 3, 2006, published as US 2006/0271016 on Nov. 30, 2006, including its prosecution history, including office communications dated Apr. 24, 2007 and Apr. 18, 2008.

U.S. Appl. No. 11/417,932, filed May 3, 2006, published as US 2006/0264910 on Nov. 23, 2006, including its prosecution history, including office communications dated Apr. 23, 2007, Apr. 21, 2008, and Dec. 19, 2008.

U.S. Appl. No. 11/417,997, filed May 3, 2006, published as US 2006/0211999 on Sep. 21, 2006, including its prosecution history, including office communications dated Jul. 31, 2006, Apr. 23, 2007, and Dec. 14, 2007.

U.S. Appl. No. 11/418,389, filed May 3, 2006, published as US 2006/0264844 on Nov. 23, 2006, including its prosecution history, including office communications dated Jan. 23, 2008.

U.S. Appl. No. 11/418,394, filed May 3, 2006, published as US 2006/0276758 on Dec. 7, 2006, including its prosecution history, including office communications dated Jul. 31, 2009.

U.S. Appl. No. 11/418,542, filed May 3, 2006, published as US 2006/0206061 on Sep. 14, 2006, including its prosecution history, including office communications dated May 21, 2007, Mar. 7, 2008, and Sep. 29, 2008.

U.S. Appl. No. 11/676,490, filed Feb. 19, 2007, published as US 2007/0224865 on Sep. 27, 2007, including its prosecution history, including office communications dated Aug. 29, 2008.

U.S. Appl. No. 11/924,484, filed Oct. 25, 2007, published as US 2008/0103482 on May 1, 2008, including its prosecution history, including office communications dated Sep. 24, 2009, May 14, 2010, and Dec. 17, 2010.

U.S. Appl. No. 12/917,412, filed Nov. 1, 2010, published as US 2011/0046572 on Feb. 24, 2011, including its prosecution history, including office communications dated Mar. 8, 2011.

* cited by examiner

NEEDLELESS MEDICAL CONNECTOR

RELATED APPLICATIONS

This application is a continuation of U.S. patent application Ser. No. 11/417,925, filed May 3, 2006, pending, which is a continuation of Ser. No. 11/157,216, filed Jun. 20, 2005, abandoned, which is a continuation of U.S. patent application Ser. No. 10/636,163, filed Aug. 7, 2003, now U.S. Pat. No. 6,916,309, which is a continuation of U.S. patent application Ser. No. 09/614,001, filed Jul. 11, 2000, now U.S. Pat. No. 6,695,817, all of which are incorporated herein by reference in their entireties.

BACKGROUND OF THE INVENTION

1. Field of the Invention

This invention relates generally to a medical valve, and in particular to a valve which, when connected between a first medical device, such as a fluid source, and a second medical device, such as a catheter, facilitates fluid flow therebetween, and when the first medical device is disconnected therefrom, induces a positive flow of fluid through the valve in the direction of the second medical device.

2. Description of the Related Art

The manipulation of fluids for parenteral administration in hospitals and medical settings routinely involves the use of connectors and valves for selectively facilitating the movement of fluids between two points. These valves are typically placed along a fluid flow line leading to a patient or other destination. For example, the tube may lead to a catheter having its tip positioned within a patient.

The valve is arranged so that a fluid source or other line may be connected thereto for providing a fluid flow from the source to the patient. When the fluid source or line is removed, the valve closes, sealing the line leading to the patient.

The element which is connected to the valve may comprise a tube or other medical device such as a conduit, syringe, IV set (both peripheral and central lines), piggyback line, or similar component which is adapted for connection to the medical valve. Unfortunately, prior art valves suffer from a problem arising from the disconnection of these medical devices from the valve.

These valves define a space within them through which a fluid or other material may flow from the device to the line on which the valve is mounted. When the medical device is connected to the valve, it typically occupies a portion of this internal valve space, displacing the fluid (whether it be a liquid or air) within the valve.

A problem arises when the medical device is disconnected from the valve. When the device is disconnected, it no longer occupies a portion of the space in the valve. The increase in space within the valve causes the fluid in the valve and line to which the valve is connected, to move to fill the space. In effect, the removal of the device creates a suction force which draws fluid into the valve.

In the medical setting, this movement of fluid is very undesirable. When the valve is connected to a fluid line leading to a patient, the movement of fluid through the line towards the space in the valve has the effect of drawing blood from the patient in the direction of the valve. A serious problem may result in that this blood may clot and clog the catheter near its tip, rendering it inoperable, and may even result in a clot of blood in the patient, which may prove fatal.

One attempt at overcoming this clogging problem has been to coat the inner surface of the catheter near its tip in order to prevent blood from sticking to its interior surfaces. This method has generally been unsuccessful in preventing clogging of the catheter.

The risk of blood clogging of the catheter is significantly heightened where the inner diameter of the catheter is small (e.g., 27 gauge). These small catheters have the advantage, however, in that they reduce the trauma and discomfort caused by insertion into a patient. Because these catheters have a very small passage therethrough, even a small suction force may draw sufficient amount of fluid back through a catheter toward the valve to introduce blood into the catheter tip, which blood may clog the catheter's passage.

Overcoming the above-stated problem is made more difficult when considering other criteria which the valve must satisfy. For example, the valve should be arranged to so that it does not have any fluid stagnation points. If the fluid is allowed to stagnate in one or more areas of the valve, bacteria growth and other problems may occur.

In addition, the valve should have an internal flow path which is smooth. Sharp edges and corners may damage blood cells and cause hemolysis.

A valve that overcomes the above-stated problems is desired.

SUMMARY OF THE INVENTION

In accordance with one preferred embodiment, a medical valve for selectively permitting fluid to flow between a first medical device and a second medical device comprises a housing that has an interface suitable for receiving a connector portion of the first medical device, and a seal. The seal is made of a flexible material and has a downstream end in fluid communication with the interface, an upstream end suitable for receiving the second medical device, and a normally substantially closed passage in fluid communication with the downstream end and the upstream end. The passage has a relatively small interior volume when in an undisturbed state and a larger interior volume upon the introduction of the second medical instrument into the upstream end of the passage. The passage retracts to define a restricted flow path and a relatively small interior volume upon the withdrawal of the second medical device from the seal (the upstream end initially being sealed as the second medical device is withdrawn) so that a fluid occupying the interior volume is forced toward the downstream end as the passage walls collapse.

In accordance with another preferred embodiment there is provided a valve seal for use in a medical valve having an interface for fluid communication with a first medical device. The seal comprises a first end in fluid communication with the interface, a second end suitable for receiving a second medical device, and at least one slit in fluid communication with the first end and the second end. The slit defines a restricted fluid flow path and a relatively small interior volume when in an undisturbed state, and defines an expanded fluid flow path and a larger interior volume upon the introduction of the second medical device into the slit. The slit retracts to define a restricted flow path and a relatively small interior volume upon the withdrawal of the second medical device from the seal.

In accordance with another preferred embodiment a method is provided for causing a positive flow in the direction of a first medical device from a valve that connects the first medical device to a second medical device and has an associated seal. The seal is adapted to receive at least a portion of the second medical device and provide fluid communication between the first and second medical devices. The method comprises the steps of withdrawing the second medical device from the seal and permitting the seal to retract from a large interior volume to a relatively small interior volume so as to displace any fluid within the seal in the direction of the first medical device.

In accordance with another preferred embodiment there is provided a method of preventing blood from flowing out of a patient into a catheter when a syringe is withdrawn from a valve between the syringe and the catheter. The method comprises the steps of connecting the downstream end of the valve to the catheter and inserting the end of the syringe into a slit forming the upstream end of a normally substantially closed seal passage that is located in a resilient seal and is in fluid communication with the downstream end of the valve. This causes the seal passage to open while providing sealing contact between the syringe and the upstream end of the seal passage. The method further comprises the steps of injecting fluid from the syringe through the seal passage to the catheter and into the patient, and withdrawing the syringe, allowing the walls of the seal passage to return to their substantially closed position while initially maintaining sealing contact between the upstream end and the syringe. This provides a force urging fluid in the passage toward the catheter.

In accordance with another preferred embodiment there is provided a medical valve for selectively permitting fluid to flow between a first medical device and a second medical device through an associated seal. The valve comprises an interface suitable for receiving a connector portion of the first medical device, and a seal holder in fluid communication with the interface.

In accordance with another preferred embodiment a system for administering fluid to a blood vessel of a patient comprises a catheter having an upstream end and a downstream end that is suitable for placement in fluid communication with the blood vessel, and a syringe suitable for expelling fluid into the catheter. The system further comprises a valve having a fitting suitable for connection to the upstream end of the catheter and providing selective fluid communication between the syringe and the catheter. The valve further comprises a seal made of a flexible material. The seal has a downstream end in fluid communication with the fitting, an upstream end suitable for receiving the syringe, and a normally substantially closed passage in fluid communication with the downstream end and the upstream end. The passage has a relatively small interior volume when in an undisturbed state and a larger interior volume upon the introduction of the syringe into the upstream end of the passage. The passage retracts to define a restricted flow path and a relatively small interior volume upon the withdrawal of the second medical device from the seal (the upstream end initially being sealed as the syringe is withdrawn), so that a fluid occupying the interior volume is forced toward the downstream end as the passage walls collapse.

In accordance with another preferred embodiment there is provided a method of making a medical valve seal of the type having a body made of a flexible material and at least one slit formed within the body between adjacent first and second slit walls. The method comprises molding first and second preforms, each preform comprising one of the first and second slit walls and a perimeter edge portion, and pressing the first and second preforms together so that the first and second slit walls face each other. The method further comprises molding an additional amount of a flexible material to at least part of the perimeter edge portions of the first and second preforms so that the first and second preforms and the additional material form a unitary mass with the slit formed therein.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which.

DETAILED DESCRIPTION OF THE PREFERRED EMBODIMENT

Figure 1:
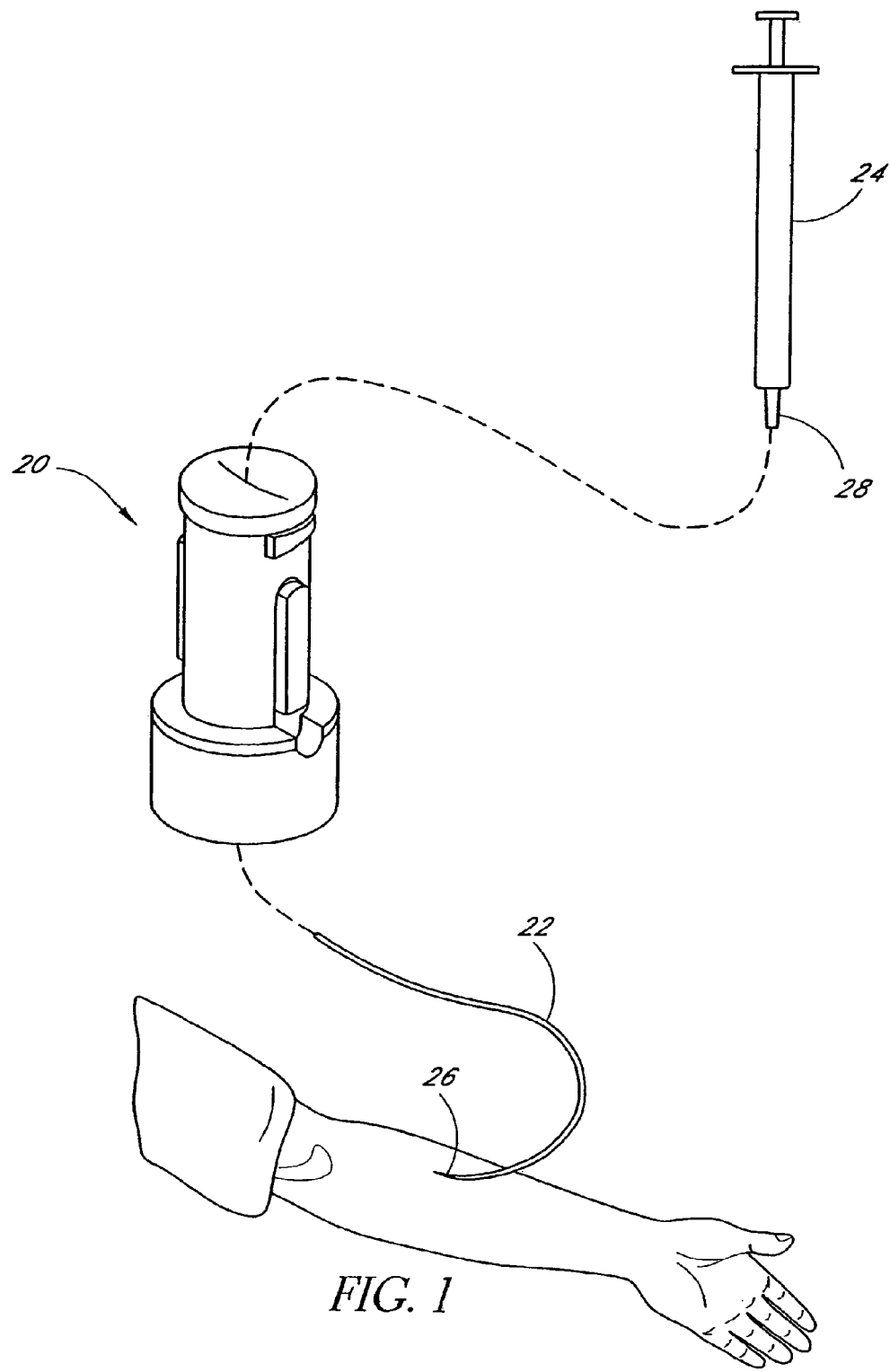
FIG. 1 is a schematic view of the use of a valve in accordance with the invention to interconnect a catheter with a fluid source such a syringe.

FIGS. 1-9 depict a valve 20 in accordance with a preferred embodiment of the invention. FIG. 1 illustrates a particular use of the valve 20 to which it is well suited. Of course, the valve 20 may be used in a variety of other manners.

As illustrated in FIG. 1, the valve 20 may advantageously be used to selectively control the flow of fluid to a first medical device (such as a catheter 22 shown here) from a second medical device (generally comprising a fluid source such as an ISO standard syringe 24). In this arrangement, the catheter 22 is connected to one end of the valve 20 and has a tip 26 inserted into the arm of a patient. The syringe 24 has a cannula tip or Luer 28 that is inserted into the other end of the valve 20, which is designed to accept the Luer 28 of the syringe 24 without a needle installed on the Luer.

When so connected, the valve 20 permits fluid to flow from the syringe 24 to the catheter 22 and into the patient. The valve 20 is also arranged so that when the syringe 24 is disconnected, fluid flow through the valve 20 is prevented. In addition, when the syringe 24 is disconnected, the valve 20 generates a "positive" fluid flow, i.e. flow of fluid in the direction of the patient, thereby preventing blood from entering the catheter 22 and causing the associated adverse effects.

Figure 2:
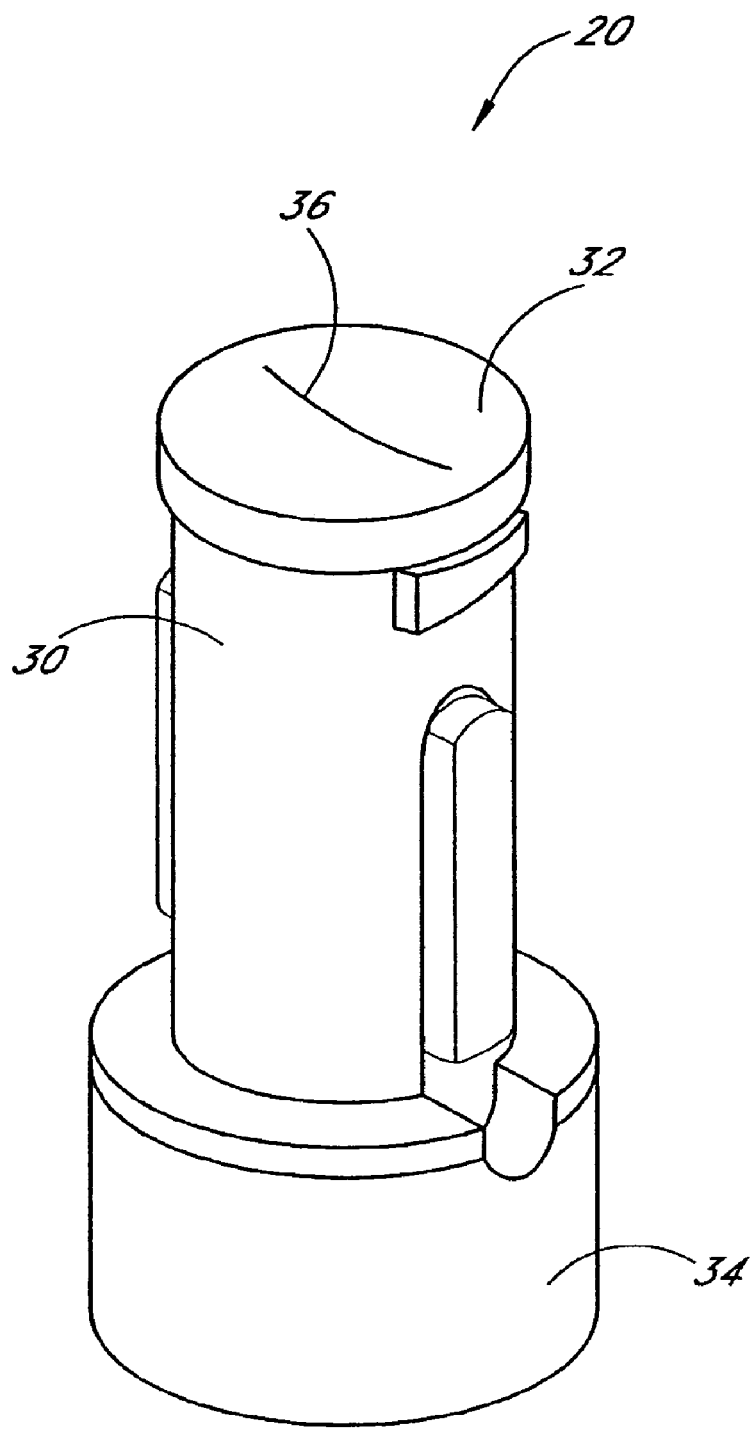
FIG. 2 is a perspective view of the valve.
Figure 3:
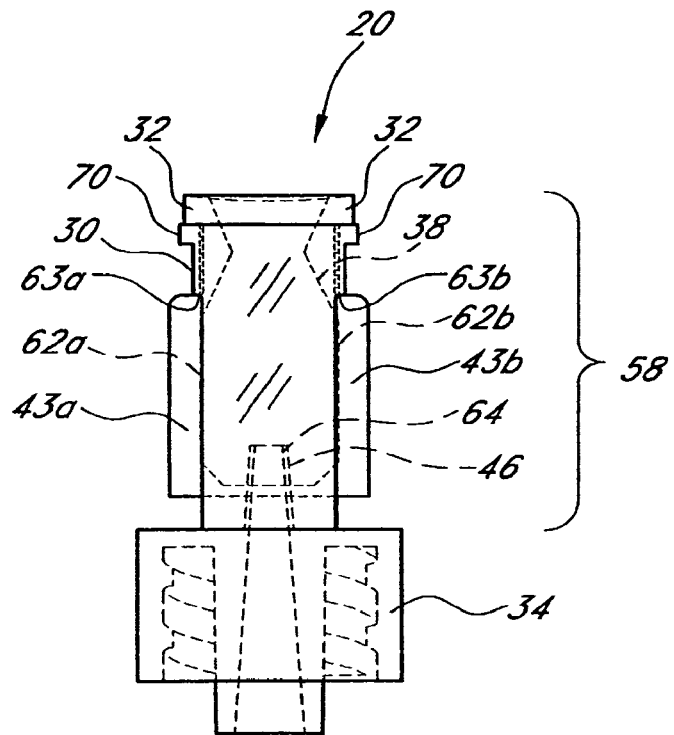
FIG. 3 is a front elevation view of the valve.
Figure 4:
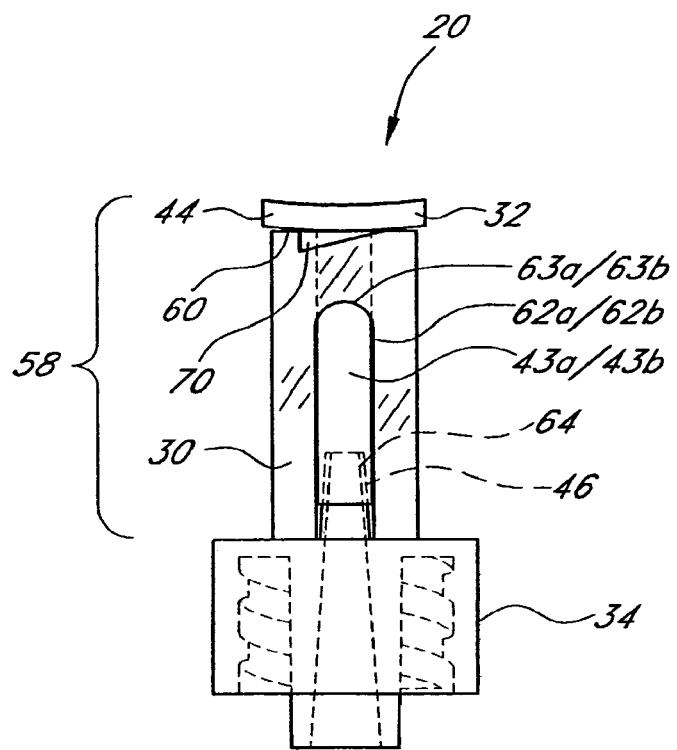
FIG. 4 is a side elevation view of the valve.
Figure 5:
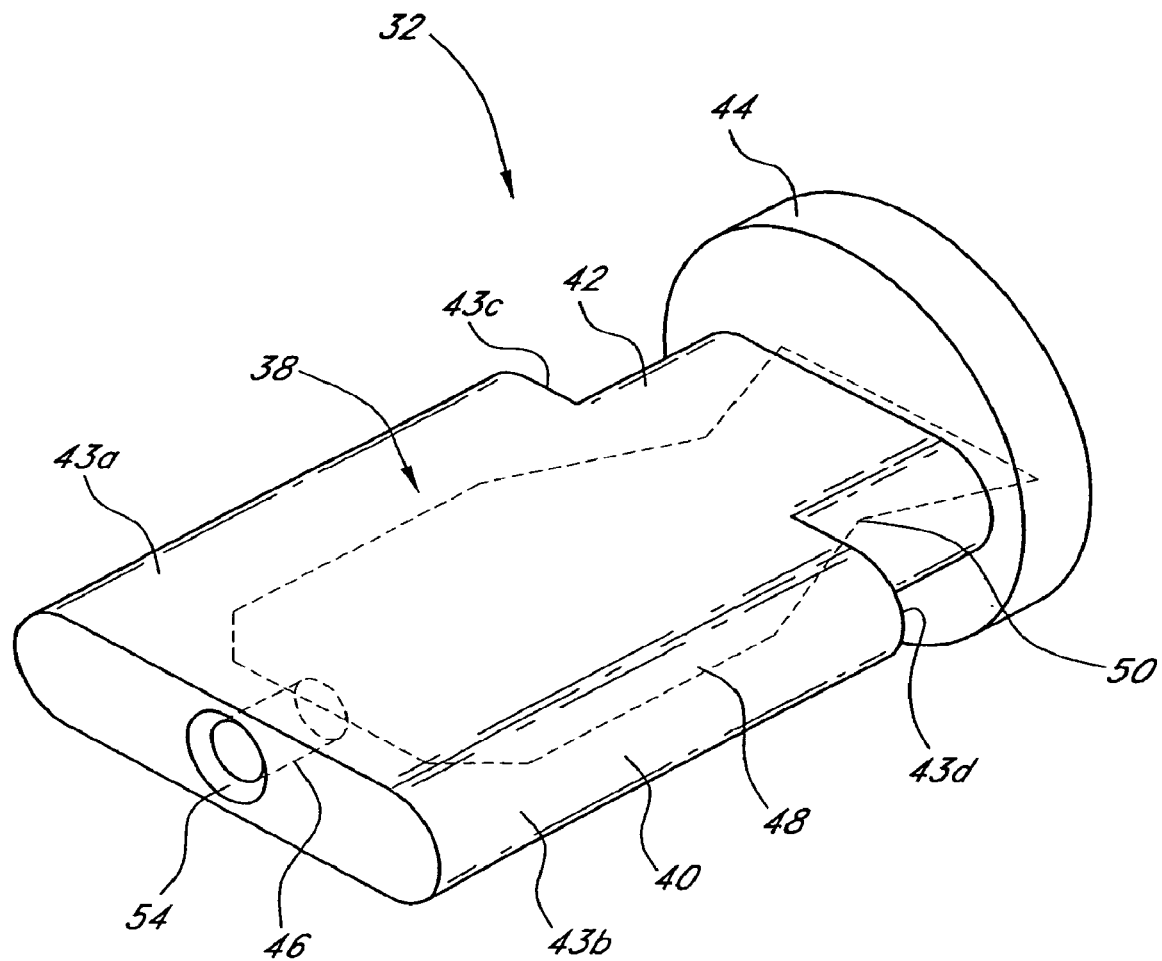
FIG. 5 is a perspective view of a seal for use in the valve.
Figures 6A, 6B:
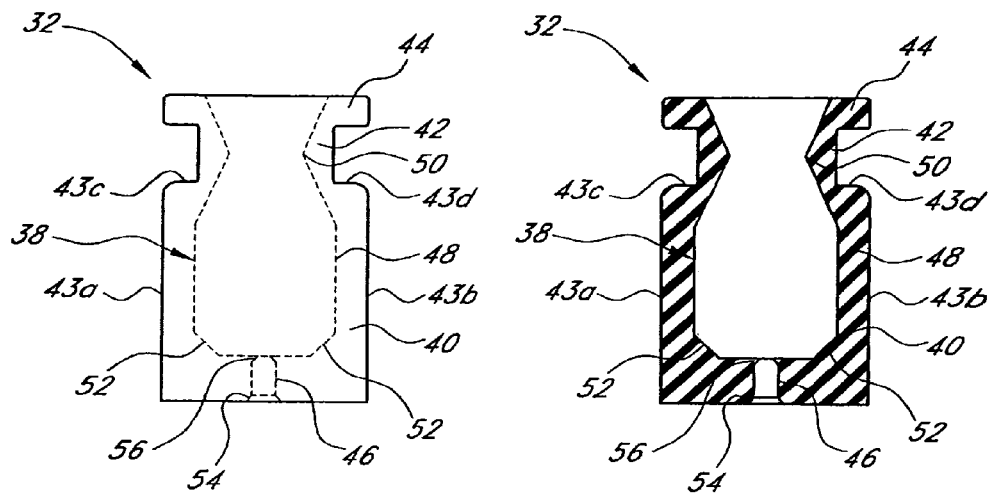
FIG. 6A is a front elevation view of the seal.
FIG. 6B is a front cross-sectional view of the seal.

FIGS. 2-4 depict one preferred embodiment of a valve 20 in accordance with the invention. The valve 20 comprises a relatively rigid housing 30 and a relatively flexible and resilient seal 32 disposed on or within the housing 30. The housing 30 has a Luer lock interface 34 at its lower end to facilitate connecting the valve 20 to a variety of medical devices. One skilled in the art will readily appreciate that a number of other interface or connection types are suitable for use in place of the Luer lock 34, such as a Luer slip connection or a barbed hose fitting.

The seal 32 has a slit opening 36 (best seen in FIG. 2) which is configured to permit the Luer 28 of a syringe 24 (see FIG. 1) to enter the seal 32 upon application of moderate pressure by the user. The syringe Luer 28 thus enters a slit 38 (see FIG. 3) formed in the interior of the seal 32. With the syringe Luer 28 thus inserted, the seal permits fluid ejected from the syringe 24 through the Luer 28 to flow through the slit 38 and Luer lock 34 and into the catheter 22 or other medical device attached to the Luer lock 34.

FIGS. 5-7B show the seal 32 removed from the housing for purposes of clarity. The seal 32 has a body 40 which may take the form of a slab having a flat, generally rectangular shape. Like the entirety of the seal 32, the body 40 is preferably formed of molded, 50 durometer silicone rubber, or is alternatively formed of synthetic polyisoprene. At one end of the body 40 is formed a flat, generally rectangular neck 42 and a generally circular transverse flange 44. The neck 42 is situated between first and second lateral extensions 43a, 43b which have shoulders 43c, 43d comprising those portions of the lateral extensions nearest the flange 44. The body 40, neck 42 and flange 44 thus form an integral unit, inside of which is formed the (preferably substantially planar) slit 38. The slit 38 extends from the slit opening 36 (best seen in FIG. 2) in the flange 44 to a lead lumen 46 formed in an end of the body 40 opposite the flange 44. The lead lumen 46 is preferably substantially cylindrical and centered about an axis that is substantially parallel to or collinear with the longitudinal axis of the seal. The slit 38 is preferably substantially planar and of virtually no thickness unless a Luer is connected. The slit 38 thus forms (in its undisturbed state, i.e. when the syringe Luer 28 has not been inserted into the seal 32) a highly restricted fluid flow path from the slit opening 36 to the lead lumen 46. As used herein in reference to a flow path, "restricted" means a flow path that permits either no fluid, or a clinically negligible amount of fluid, to pass.

The preferred configuration of the slit 38 and lead lumen 46 is best seen in FIGS. 6A-7B. The slit 38 has a body portion 48 within the body 40 of the seal 32. Advantageously, the body portion 48 is a region of maximum width, preferably about 0.228" of the slit 38. The slit 38 tapers to a point or region 50 of minimum width, which is preferably located within the neck 42. Advantageously, at the region 50 of minimum width the slit 38 is preferably about 0.120" wide. In other words, the width of the slit 38 in the body portion 48 is almost twice that of the region 50 of minimum width. From the region 50 of minimum width the slit 38 tapers outward to the slit opening 36, where it attains a preferred width of about 0.200". This tapered configuration acts as lead-in for insertion of the syringe Luer 28 into the slit 38. The slit 38 may also have beveled corners 52 at its lower end, opposite the neck 42. At its lower end the slit 38 connects to the lead lumen 46 to facilitate fluid communication between the slit 38 and the lead lumen 46. The lead lumen 46 preferably has a lead-in chamfer 54 and a beveled transition 56 to the slit 38. The preferred inside diameter of the lead lumen 46 is about 0.040".

Figures 7A, 7B:
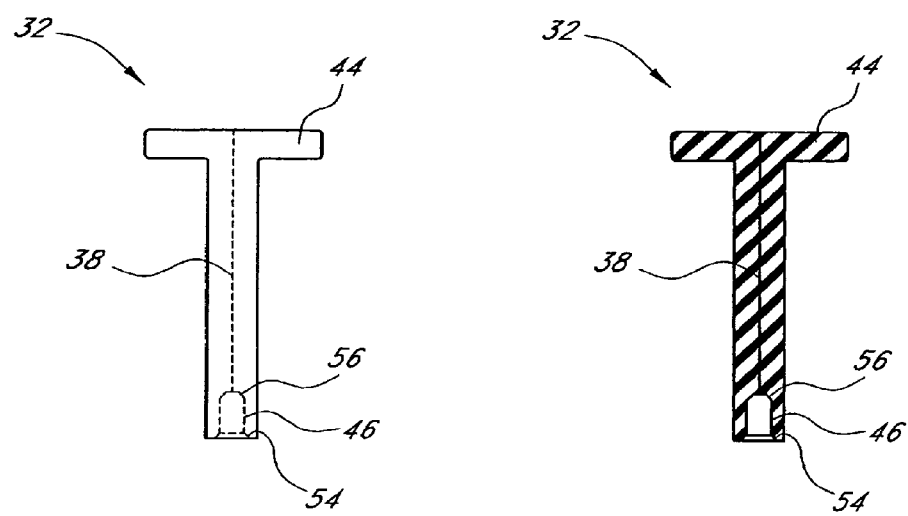
FIG. 7A is a side elevation view of the seal.
FIG. 7B is a side cross-sectional view of the seal.

In the side views of FIGS. 7A and 7B, it may be seen that the seal 32 has a T-shaped cross section before installation in the housing 30, with the flange 44 forming the cross portion of the "T". Viewed from the side, the slit 38 is uniformly thin, i.e. of no or virtually no thickness, as it runs from the top of the seal 32 to the lead lumen 46. However, upon installation in the housing 30, the thickness of the slit 38 (when viewed from the side) will vary somewhat as will be explained in greater detail below.

Figure 8A:
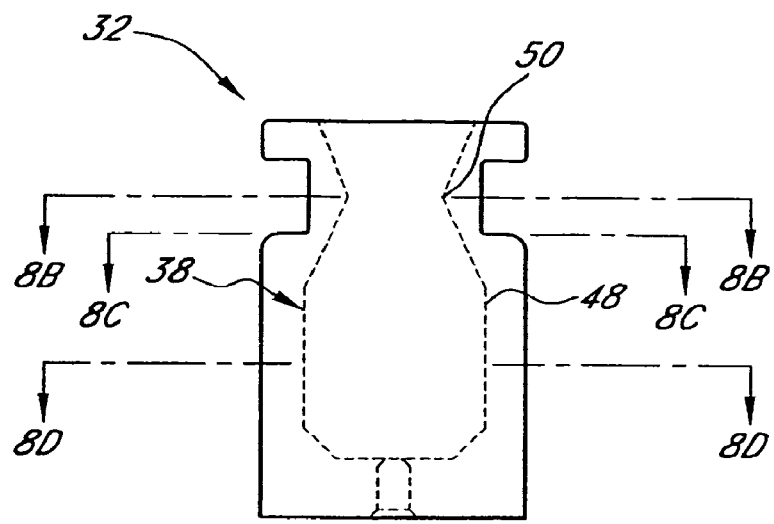
FIG. 8A is a front elevation view of the seal.
Figure 8B:
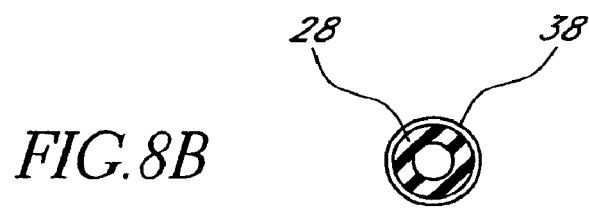
FIGS. 8B-8D are cross-sectional schematic views of the insertion of a medical device into the seal taken through lines 8B-8B, 8C-8C and 8D-8D of FIG. 8A, respectively.

FIGS. 8A-8D show the effects, in terms of sealing performance, of the varying width of the slit 38 after introduction of a syringe Luer 28 into the slit 38. (The syringe Luer 28 is not shown in FIG. 8A for purposes of clarity.) FIG. 8B shows the arrangement of the slit 38 and the syringe Luer 28 at the region 50 of minimum width, when the Luer 28 has been fully inserted into the slit 38. Due to the relative narrowness of the slit 38 at the region 50, the slit 38 draws up against substantially the entire perimeter of the syringe Luer 28 at that location, creating a relatively tight perimeter seal between the slit 38 and the Luer 28. In other words, the perimeter of the open slit 38 at the region 50 is less than the circumference of the Luer 28.

Figure 8C:
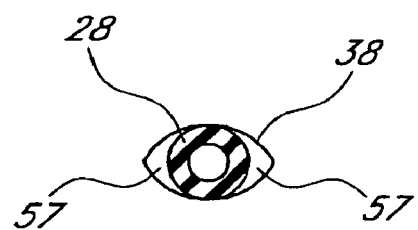
Figure 8D:
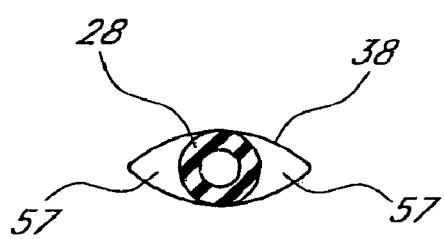

FIGS. 8C and 8D show that where the slit 38 is wider (i.e., in the body portion 48 of the slit and the transition from the region 50) the slit no longer contacts the entire perimeter of the syringe Luer 28, leaving gaps 57 on one or both sides and the end of the Luer 28. In other words, the perimeter of the open slit in the body portion 48 is greater than the circumference of the Luer 28. As will be discussed in greater detail below, this arrangement of a slit-Luer seal near the top of the slit 38 and a fluid-occupiable volume (in the form of the gaps 57) below the slit-Luer seal, promotes a positive-flow function for the valve 20 when the syringe Luer 28 is withdrawn.

Figure 9:
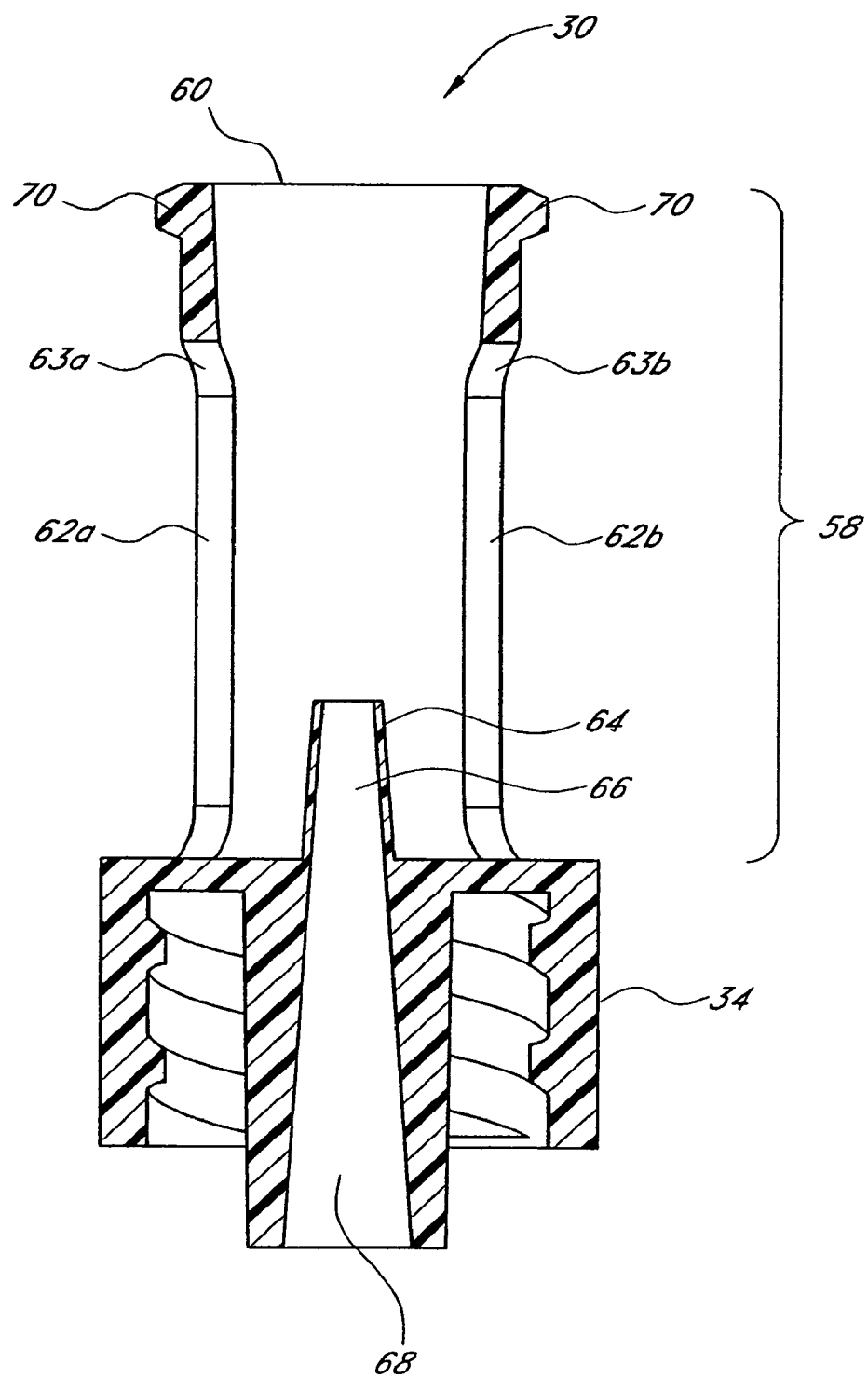
FIG. 9 is a front cross-sectional view of a housing for use in the valve.

FIGS. 3, 4, and 9 show a preferred configuration of the housing 30 and the installation of the seal 32 therein. The housing 30 is preferably formed of molded polycarbonate, or alternatively formed from any suitable thermoplastic. The housing 30 has a seal holder 58 attached to the Luer lock 34; the seal holder preferably has a cylindrical configuration, but may comprise any shape or construction sufficient to hold the seal 32 on or in the housing 30 without interfering with operation of the valve 20. The seal holder has an axial opening 60 opposite the Luer lock 34, and first and second side openings 62a, 62b which have first and second top edges 63a, 63b that comprise the edges of the side openings nearest the axial opening 60. A lead cannula 64 (best seen in FIG. 9) extends from the Luer lock 34 toward the axial opening 60 and contains an internal lumen 66 which is in fluid communication with a lumen 68 in the Luer lock 34. The lead cannula 64 is preferably substantially cylindrical or frusto-conical in shape and centered about an axis that is substantially parallel to or collinear with the longitudinal axis of the housing 30. A pair of lugs 70 are positioned on the end of the seal holder 58 near the axial opening 60, to permit a Luer lock or other threaded connection (not shown) to threadably engage the housing 30 at the axial opening 60.

As best seen in FIGS. 3 and 4, most of the seal 32 is situated within the seal holder 58, with the first and second lateral extensions 43a, 43b of the seal 32 protruding from the first and second side openings 62a, 62b. The lead lumen 46 of the seal 32 is situated so that the lead cannula 64 extends at least partway into the lead lumen, facilitating fluid communication between the seal 32 and the Luer lock 34. The flange 44 covers the axial opening 60 and contacts the adjacent edges of the opening. Preferably, the distance between the axial opening 60 and the top edges 63a, 63b of the side openings 62a, 62b is slightly larger than the distance between the flange 44 and the shoulders 43c, 43d of the lateral extensions 43a, 43b. This arrangement results in the application of a tensile force or preload to the seal 32 between the flange 44 and the lateral extensions 43a, 43b. The preload arises as the shoulders 43c, 43d bear against the top edges 63a, 63b and the flange 44 bears against the edges of the axial opening 60. The preload causes the flange 44 to assume a slightly bowl-shaped or concave configuration as the edges of the axial opening 60 bear against the underside of the flange 44. The bowl-shaped flange 44 thus serves as a lead-in for the insertion of the syringe Luer 28 into the slit opening 36 (best seen in FIG. 2), and tends to pinch closed the slit opening 36 and thus enhances the ability of the seal 32 to prevent fluid flow. The preload also prevents buckling of the seal along its longitudinal axis and maintains the sides of the slit 38 in close proximity along their entire length. The preload thus promotes a relatively thin slit below the flange 44, which enhances the sealing performance of the slit 38.

Figure 10:
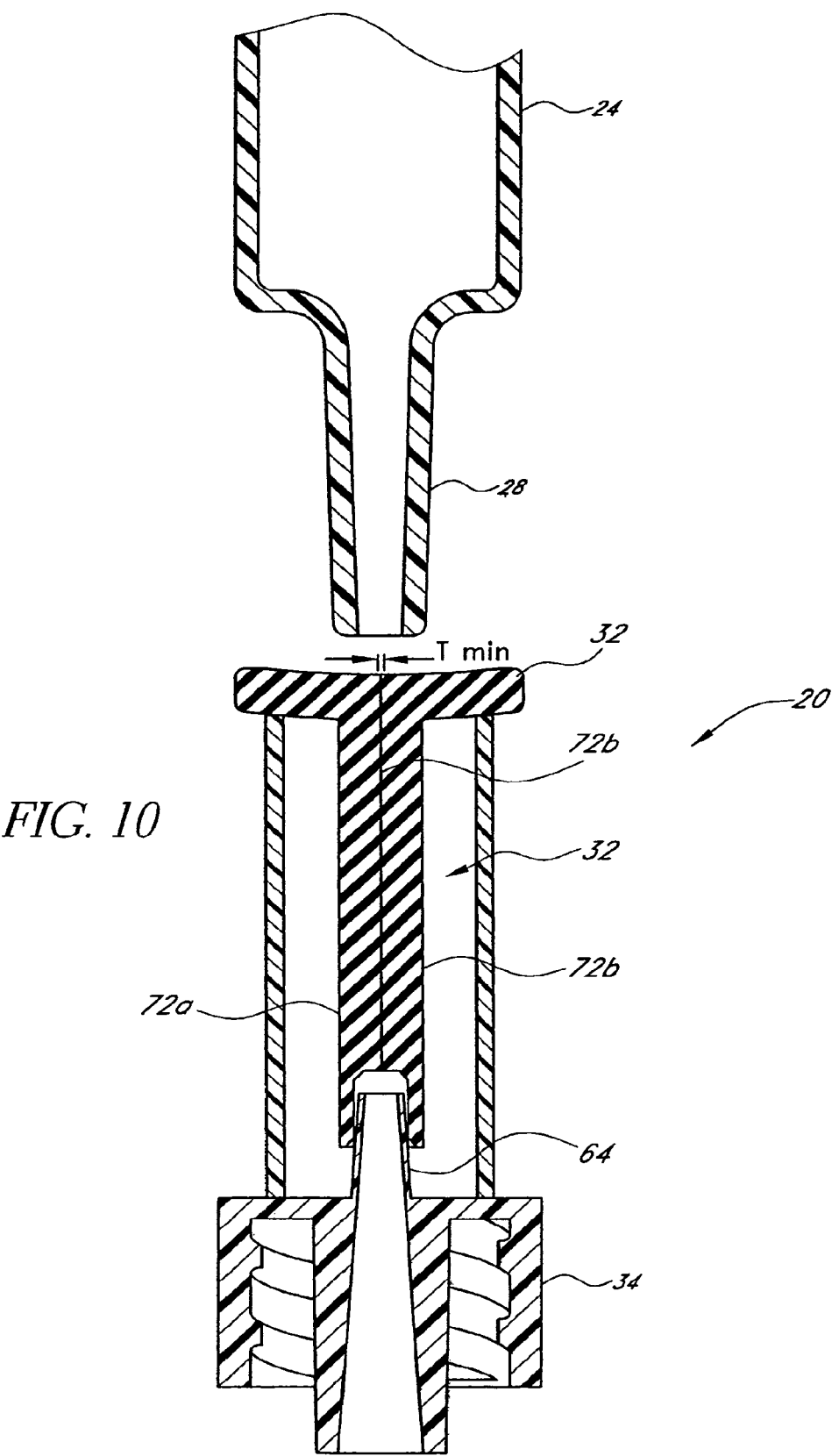
FIG. 10 is a side cross-sectional view of the valve and the syringe before insertion of the syringe into the valve.

FIGS. 10-14 illustrate the function of the valve 20 as a syringe Luer 28 is inserted into and withdrawn from the slit 38. FIG. 10 shows the valve 20 prior to insertion of the syringe Luer 28; at this point the slit 38 defines a substantially closed or highly restricted flow path through the seal 32, marked by a very thin (or substantially nonexistent) path thickness $T_{min}$ between slit walls 72a, 72b. This thin or nonexistent path thickness $T_{min}$ prevails along most or substantially all of the length of the slit 38 below the flange 44. This condition restricts fluid flow through the seal 32 so as to seal off the catheter 22 (see FIG. 1) or other medical device connected to the Luer lock 34. At this point the slit 38 also defines a relatively small interior volume $V_{min}$ within the seal 32, between the slit walls 72a, 72b. (As used herein in reference to an interior volume of the seal, "relatively small" means a volume that is either nonexistent or clinically negligible in size.) In this initial state, the seal 32 is situated upon the lead cannula 64 such that substantially none of the lead cannula 64 extends into the slit 38.

Figure 11:
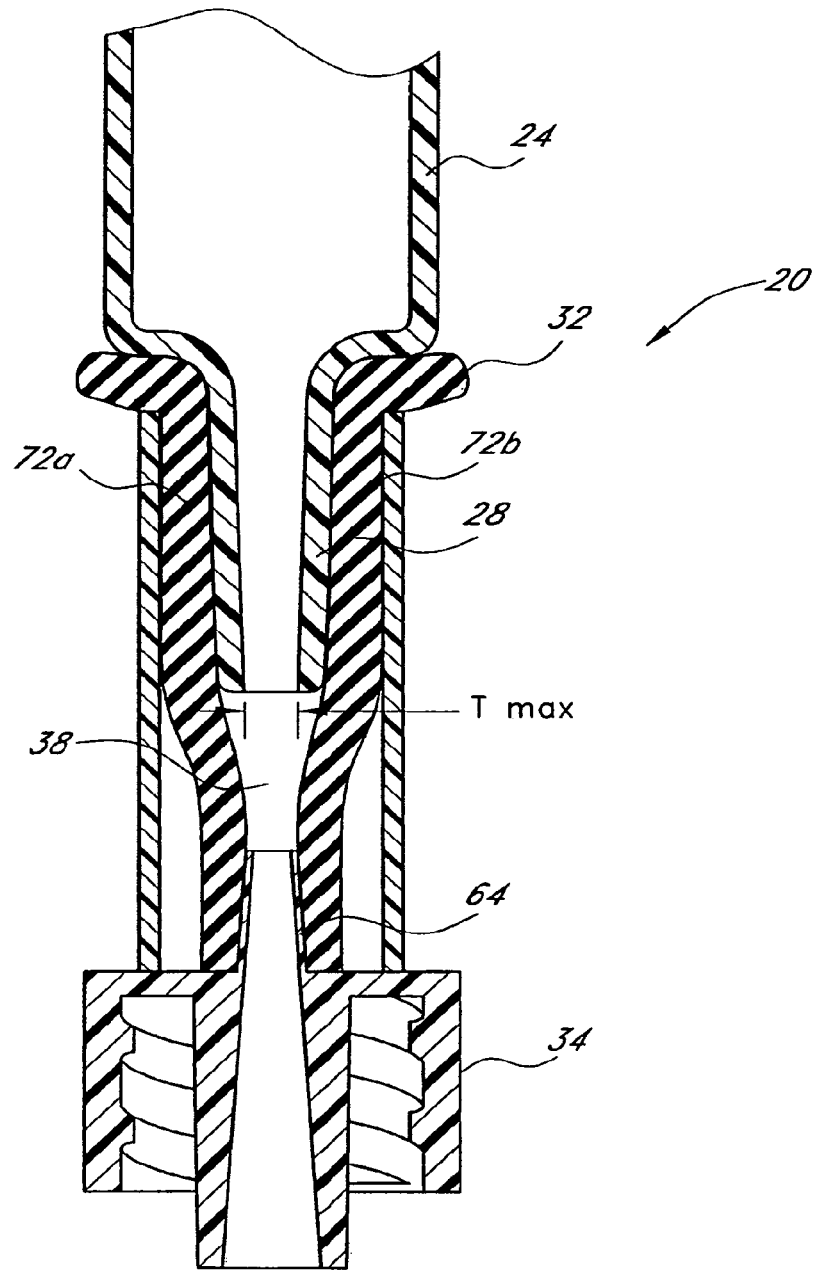
FIG. 11 is a side cross-sectional view of the valve with the syringe fully inserted.
Figure 12:
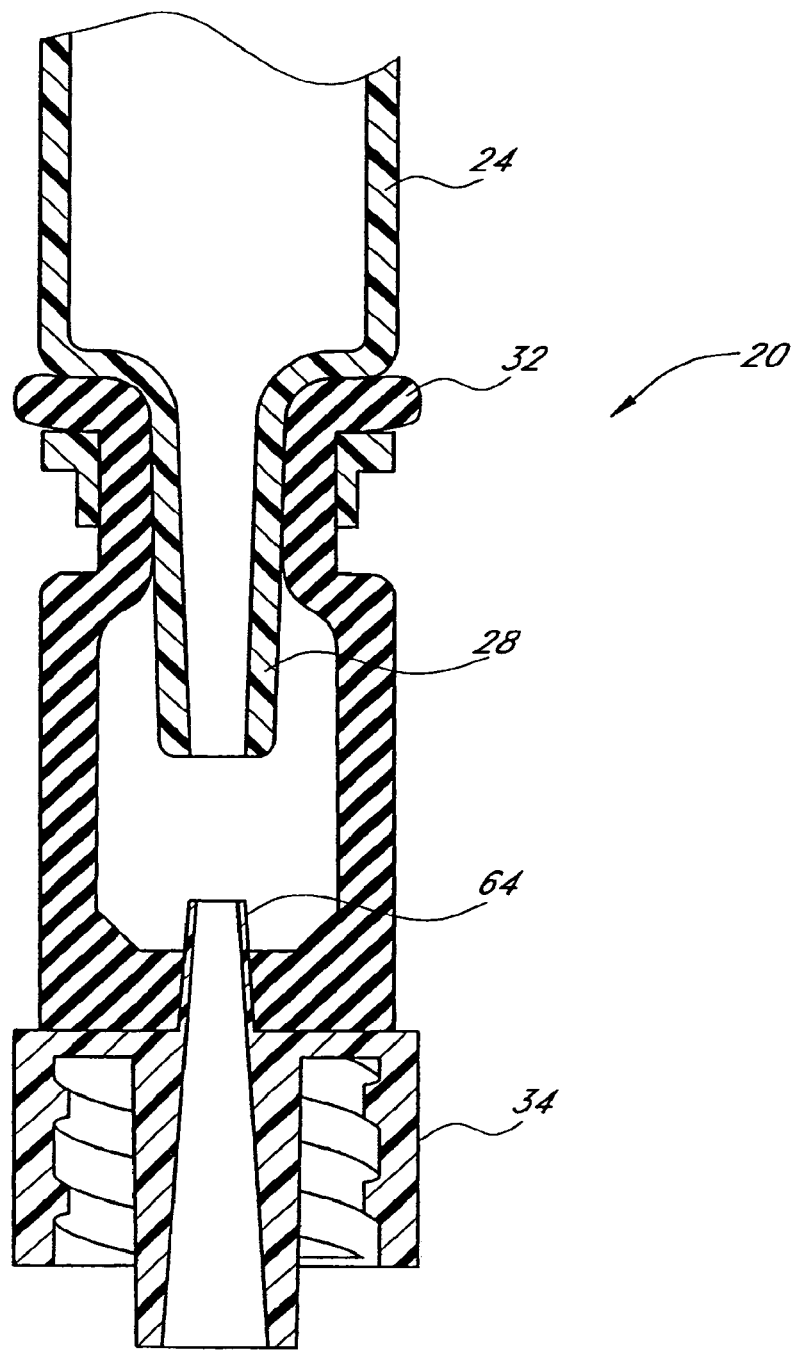
FIG. 12 is a front cross-sectional view of the valve with the syringe fully inserted.

FIGS. 11 and 12 show the valve 20 after the syringe Luer 28 has been completely inserted into the slit 38. The seal 32 has also been stretched or forced downward onto the lead cannula 64, at least part of which penetrates into the slit 38 itself. At this point the slit 38 defines an expanded flow path through the seal 32, in that the slit walls 72a, 72b have spread to a path width $T_{max}$. The seal 32 thus permits fluid to flow between the syringe 24 and the catheter 22. In addition, the slit 38 now defines a larger or maximum interior volume $V_{max}$. $V_{max}$ comprises the entire space between the slit walls 72a, 72b less the volume taken up by the cannula (but not the internal lumen) of the syringe Luer 28 and less that portion of the lead cannula 64 which has penetrated into the slit 38. Accordingly, under pressure exerted via the syringe 24 an amount of fluid substantially equivalent to $V_{max}$ now fills the slit 38 between the slit walls 72a, 72b. This is also shown as gaps 57 in FIGS. 8C and 8D.

Figure 13:
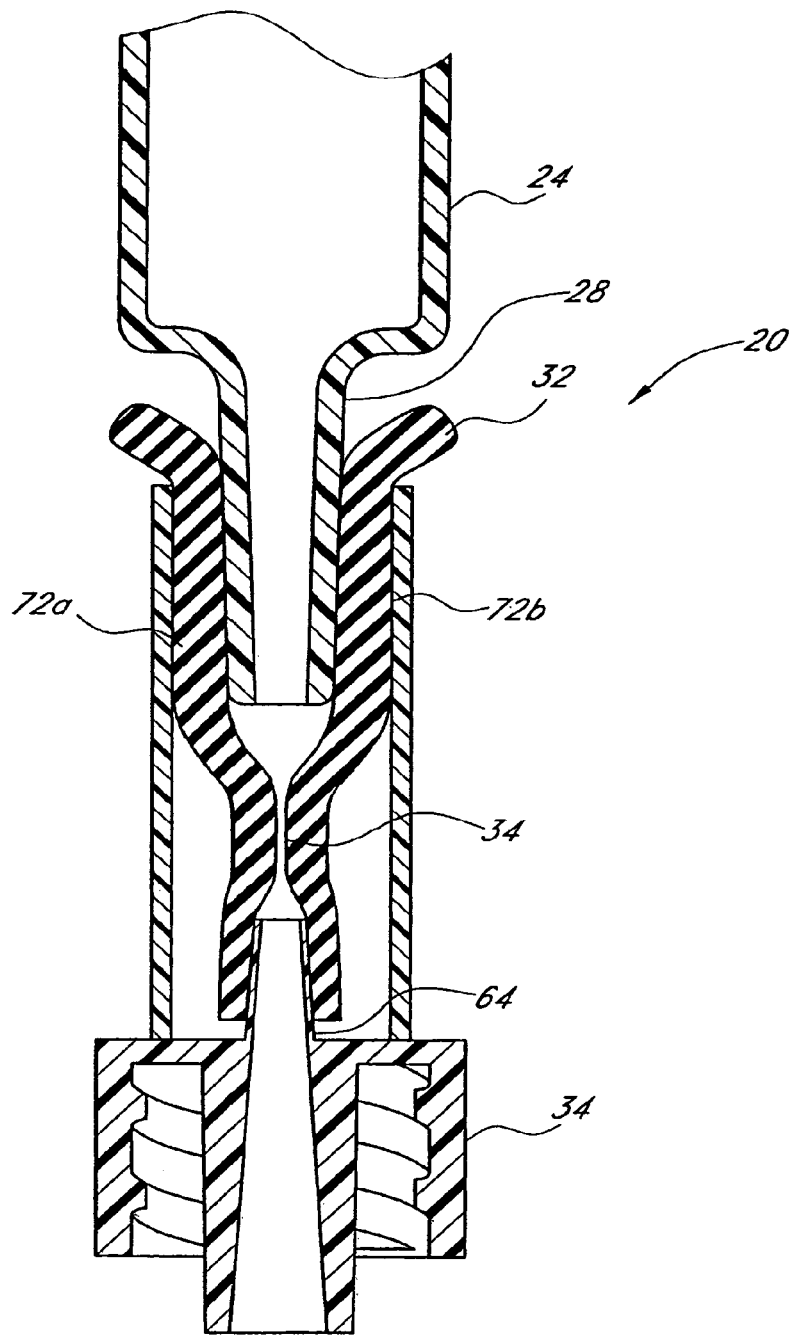
FIG. 13 is a side cross-sectional view of the valve with the syringe partly withdrawn.
Figure 14:
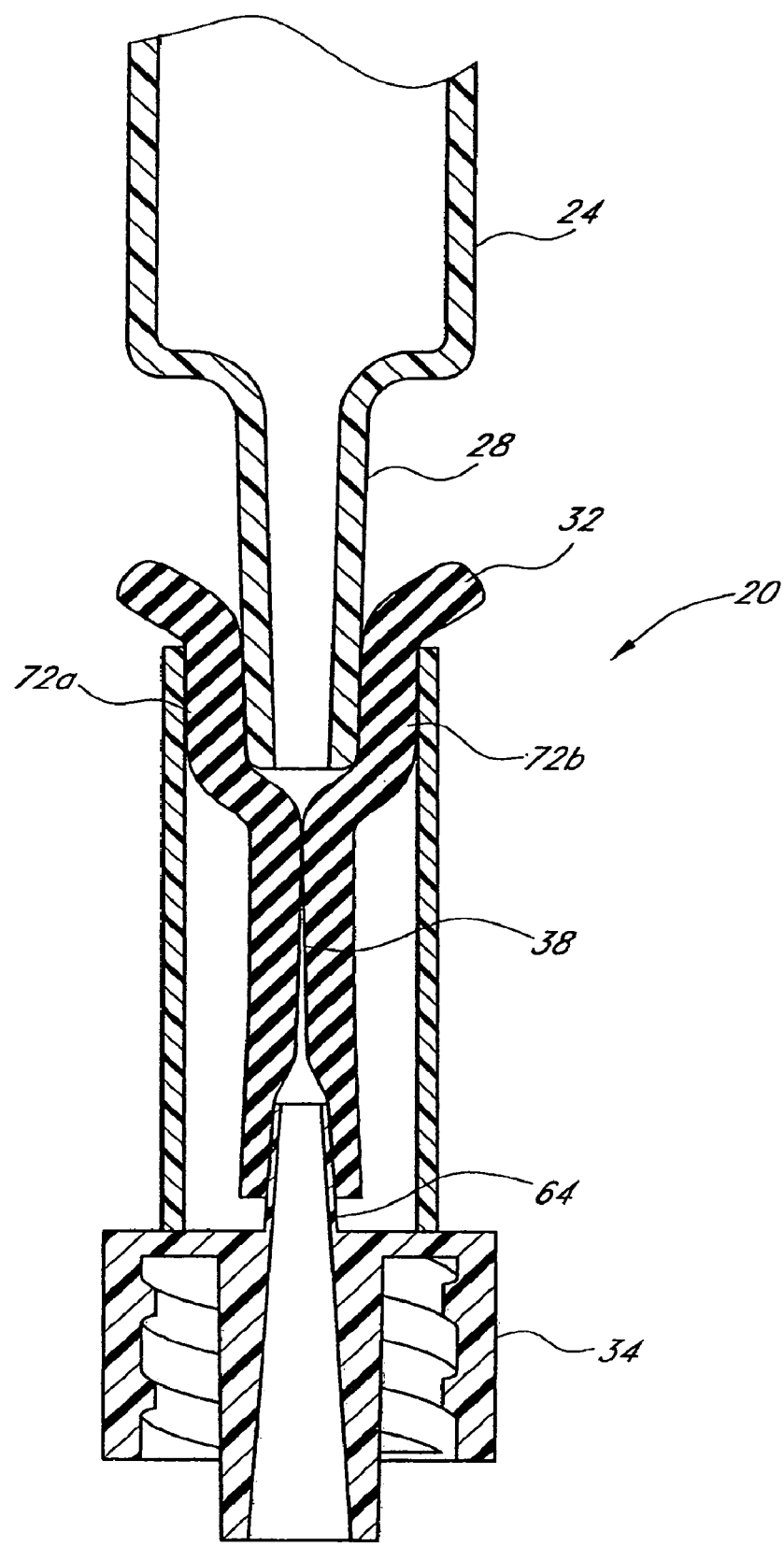
FIG. 14 a side cross-sectional view of the valve with the syringe further withdrawn in comparison to FIG. 13.

FIGS. 13 and 14 show the function of the slit 38 as the syringe Luer 28 is withdrawn from the valve 20. As the syringe Luer 28 and lead cannula 64 exit the slit, the slit walls 72a, 72b retract to substantially their original configuration to once again define a narrow path width (approaching $T_{min}$) between them. This retraction of the slit walls 72a, 72b reduces the volume between the walls; that is, the internal volume within the slit 38 is decreasing from $V_{max}$. Thus the amount of fluid within the slit must also decrease from V. Accordingly, the retracting slit walls 72a, 72b displace the fluid from the slit 38 as the syringe Luer 28 is withdrawn.

The fluid thus displaced cannot flow out of the slit 38 through the top of the seal 32. As detailed above with regard to FIGS. 8A-8B, the slit 38 maintains a tight seal against the syringe Luer 28 at the region 50 of minimum width as the syringe Luer 28 is withdrawn. In addition, the displaced fluid cannot flow into the interior of the syringe 24 at all times relevant to the use of the valve 20. Therefore, substantially all of the displaced fluid must exit the slit 38 through the lead cannula 64 and Luer lock 34, resulting in positive flow from the valve 20 upon withdrawal of the syringe Luer 28.

Figure 15:
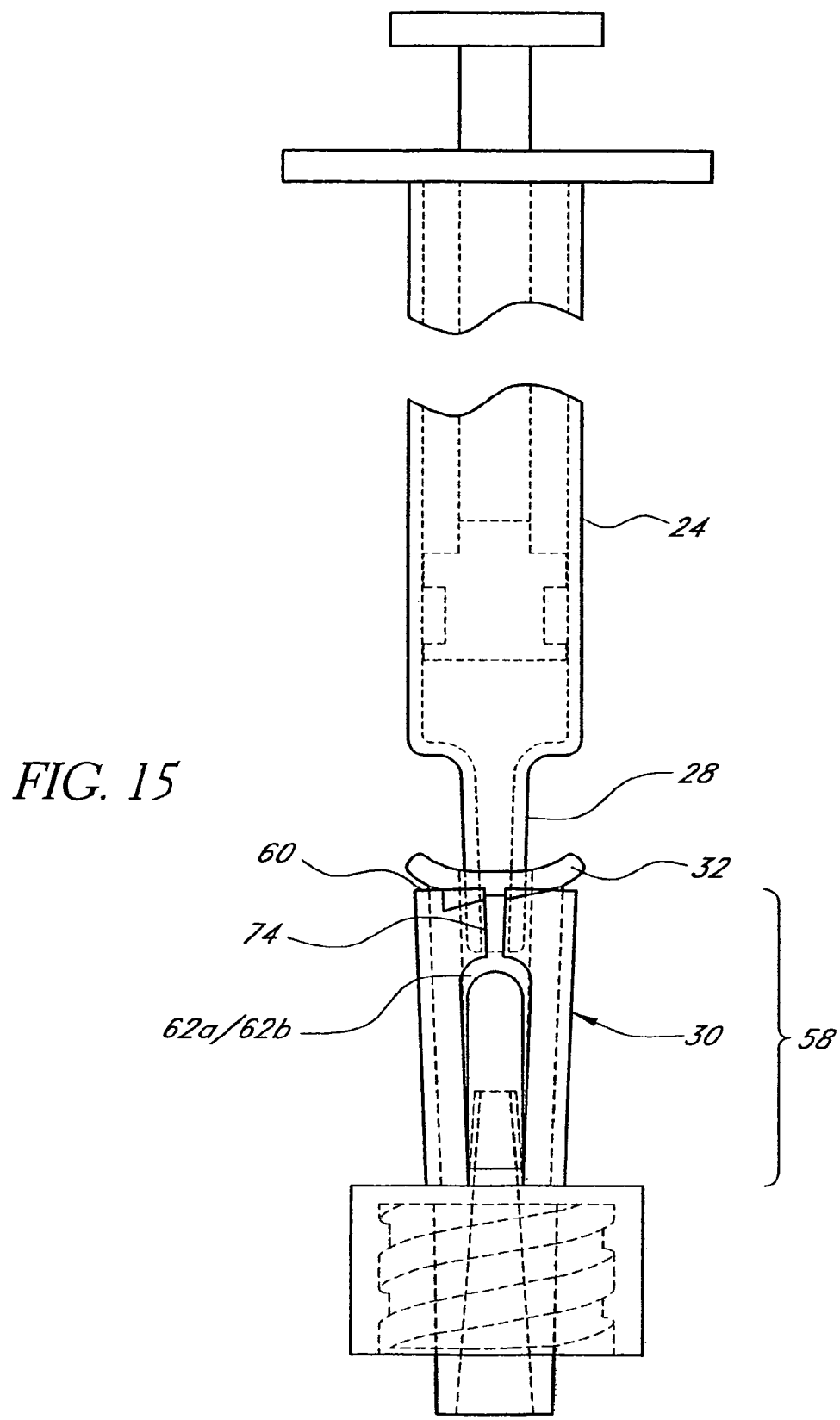
FIG. 15 is a side elevation view of an alternative embodiment of the valve, with the syringe partly inserted.
Figure 16:
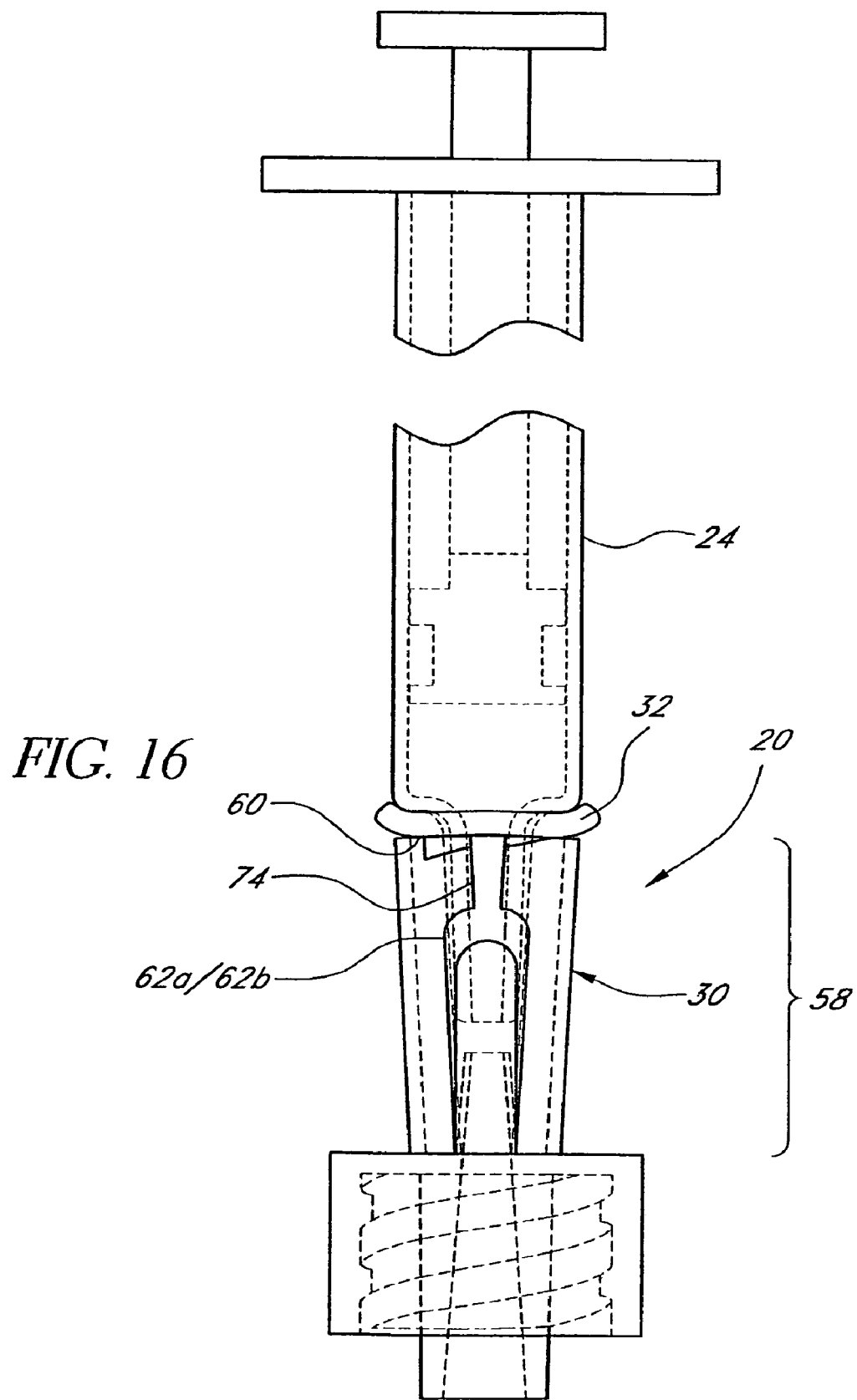
FIG. 16 is a side elevation view of an alternative embodiment of the valve, with the syringe fully inserted.
Figure 17:
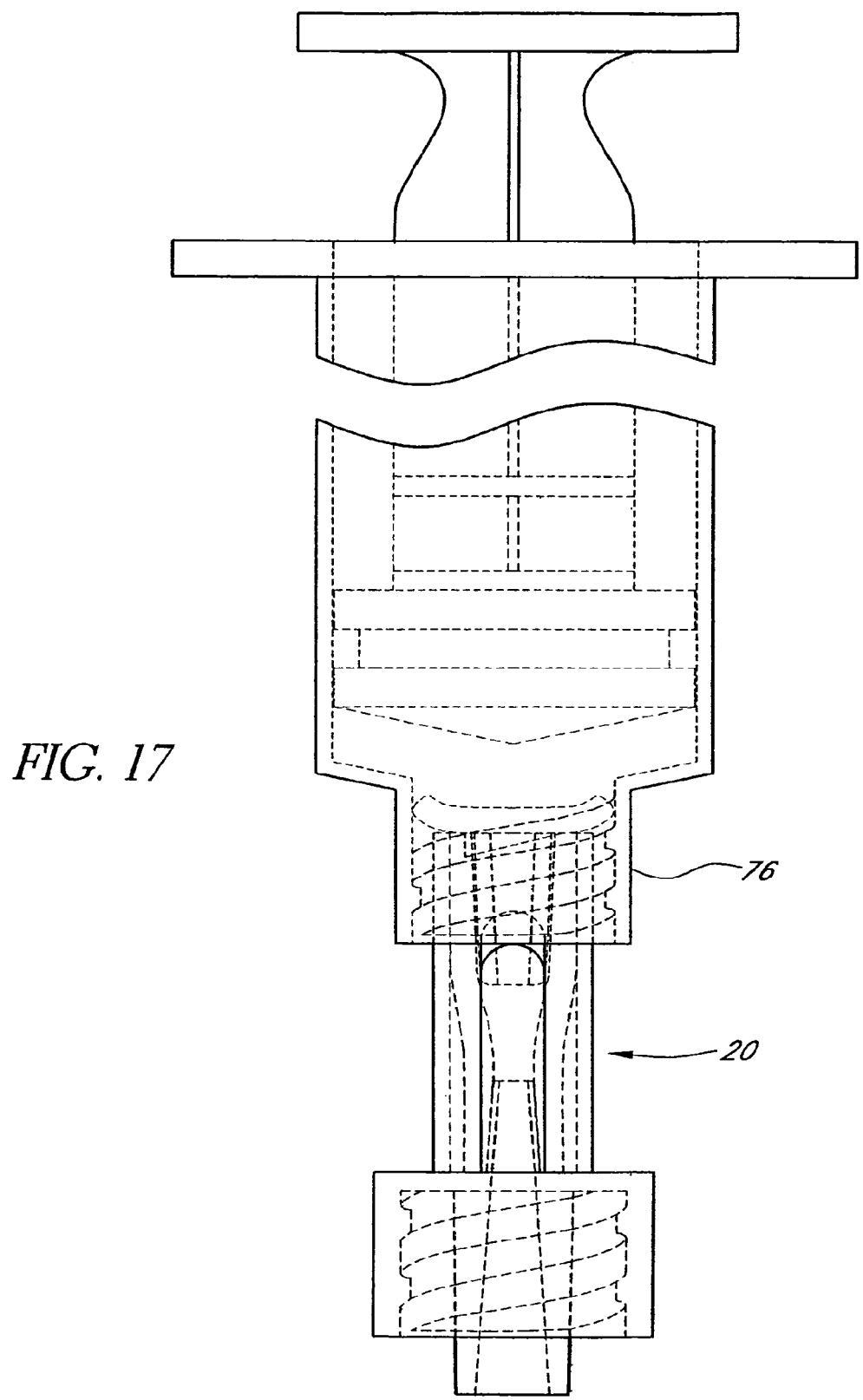
FIG. 17 is a front elevation view of the valve as used with a syringe having a Luer lock.

FIGS. 15-18 show variations on the valve 20 disclosed above, which variations may be desirable under certain operating conditions. For example, as seen in FIGS. 15 and 16 the housing 30 may have a break 74 running vertically between the axial opening 60 and one or both of the side openings 62a, 62b. The break 74 permits the seal holder 58 to spread open as a Luer slip 28 (as opposed to a Luer lock 76 shown in FIG. 17) is inserted into the seal 32. This spreading action has been found to be advantageous for using the valve 20 with a Luer slip 28, as the valve 20 becomes less likely to squeeze or pinch the Luer 28 out of the seal 32.

Figure 18:
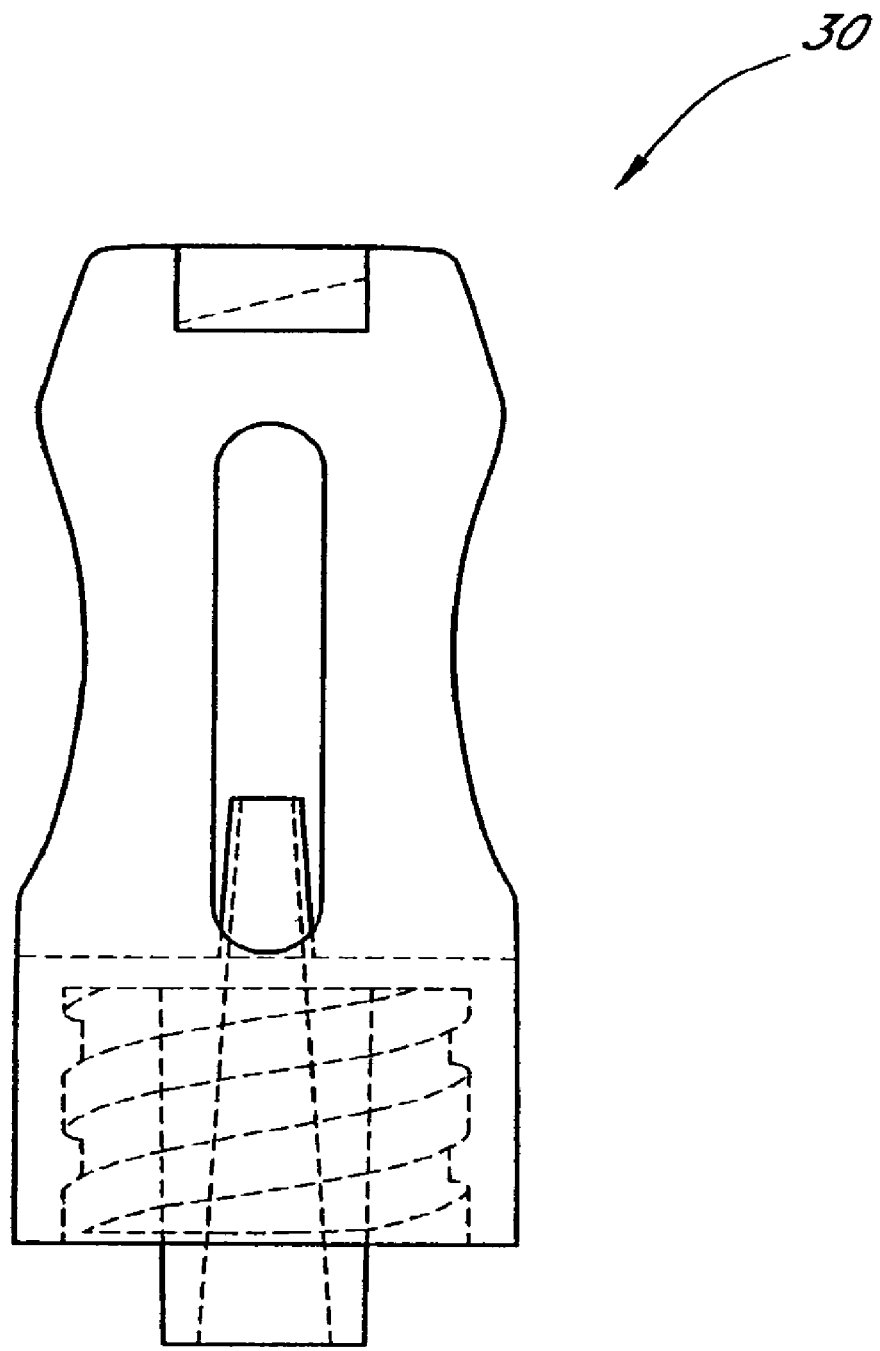
FIG. 18 is a side elevation view of an alternative embodiment of the valve housing.

FIG. 18 shows an alternative configuration of the housing 30, with a curved or streamlined appearance in comparison to the housing disclosed above. Both this type of housing or the type disclosed above, may have an external coating or layer of a relatively soft, pliant material such as a thermoplastic elastomer to enhance operator comfort and to promote the theme of a valve 20 that provides a connection without the use of sharp, puncturing elements such as needles or blades.

FIGS. 19A-21 depict a preferred method of making the seal 32. First, a pair of preforms 202a, 202b are molded between first and second mold pairs 204a, 204b and 206a, 206b respectively. Each preform 202 has a generally planar portion 208 that, in the completed seal 32, forms a wall of the slit 38 (see FIGS. 6A-7B). A flange portion 210 is also integrally molded into both preforms 202. The sides of the flange portion 210 are preferably set back from the upper face of the planar portion 208, to provide a space for overmold material (discussed in further detail below) to flow between and connect the flange portions 210. The molding of the preforms 202 is accomplished using conventional techniques and equipment, preferably by injecting a thermoset material into the cavity formed between the mold pairs 204a, 204b and 206a, 206b and heating the molds and/or material to the set temperature of the specific material used. Pressure may be applied as needed to prevent material from leaking between the halves of the mold.

Figure 19A:
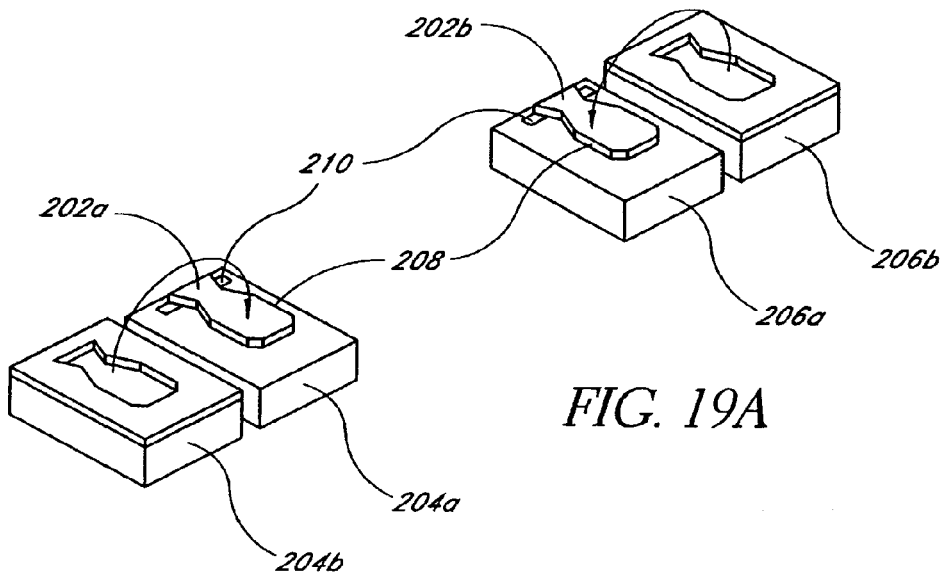
FIGS. 19A-19E are schematic views of a process of making the seal.
Figure 19B:
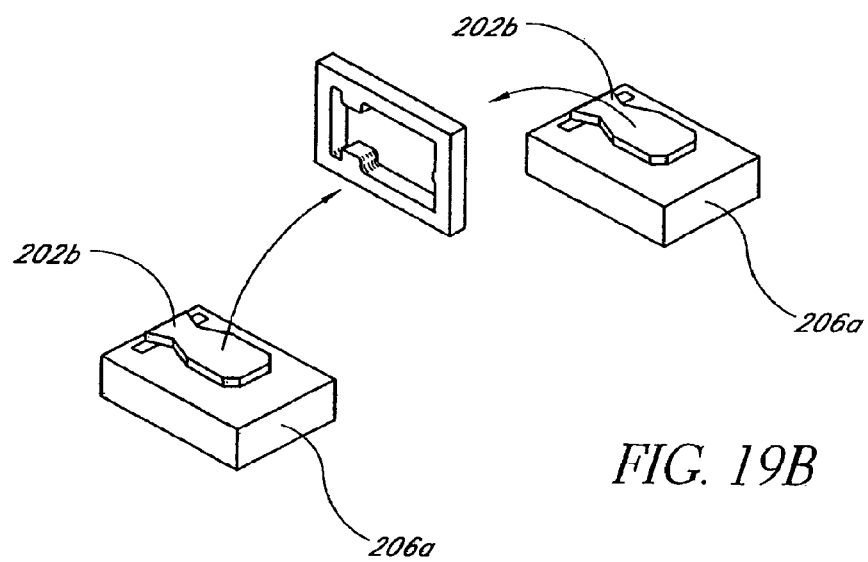
Figure 19C:
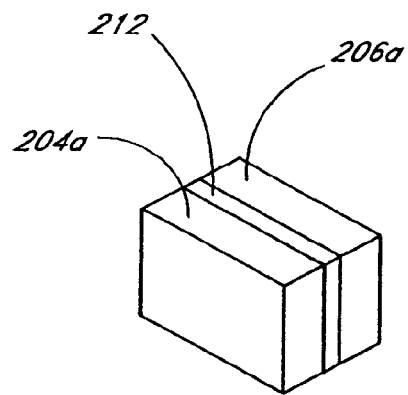

After this initial molding step, the mold halves 204a, 206a, with the preforms 202a, 202b still positioned in them, are pressed together with an overmold plate 212 positioned between the mold halves, as depicted in FIGS. 19B-19C. The overmold plate 212, best seen in FIG. 20 (with the outline of the preforms 202 also shown in phantom), comprises a generally planar plate body 214 with an overmold opening 216 cut into the body 214. The overmold opening 216 has a plan perimeter that conforms to the outer edges of the completed seal 32, and may include a mandrel 218 that projects from the lower portion of the opening 216 and forms the lead lumen 46 (see FIGS. 6A-7B) during the overmold process, as will be discussed in greater detail below. The contacting faces of the mold halves 204a, 206a and the overmold plate 212 are advantageously substantially planar. Thus the mold halves 204a, 206a, plate 212, and preforms 202a, 202b define a mold cavity or volume 220 between the walls of the overmold opening 216 and the outer edges of the preforms 202a, 202b, and between the faces of the mold halves 204a, 206a.

With the mold apparatus (mold halves 204a, 206a and overmold plate 212) arranged as shown in FIG. 19C, additional thermoset material is injected into the mold apparatus to fill the mold cavity 220 and form the remainder of the seal 32. Preferably, the additional material is injected soon (i.e., a few seconds) after the preforms 202 are molded and while they are still somewhat hot from the initial molding. The additional material injected into the mold cavity 220 bonds to the edges of the preforms 202 and forms the edges of the slit 38 in the completed seal 32. In other words, the remainder of the seal is overmolded onto the "sandwich" of preforms 202. Preferably, the preforms 202 are pressed together with sufficient force during the overmolding process to prevent the additional material from migrating between the contacting surfaces of the preforms 202. This preserves the patency of the slit 38 by preventing the contacting faces of the preforms 202 from bonding to each other during the overmold step.

The overmold plate 212 may be made with a thickness approximately the same as that of the "sandwich" of preforms 202a, 202b to define a mold cavity 220 that, as described above, comprises the open space between the walls of the overmold opening 216 and the outer edges of the preforms 202a, 202b, and between the faces of the mold halves 204a, 206a. This overmold opening thus also has a thickness approximately equal to that of the preform sandwich, and all or nearly all of the overmold material injected therein bonds only to the edges of the preforms 202a, 202b. In an alternative embodiment, the overmold plate 212 may have a thickness greater than the preform sandwich. This thicker, alternative overmold plate thereby defines a mold cavity that also includes open space that is created between the mold halves 204a, 206a and the outer (i.e., facing away from the slit in the completed seal) faces of the preforms 202a, 202b. The mold halves 204a, 206a are preferably configured with projections, ridges, channels, gaps or the like to create such space during this alternative overmold step while pressing the preforms together as may be needed during the overmold. Accordingly, in this embodiment the overmold material bonds to both the edges and to the outer faces of the preforms 202a, 202b. In other words this alternative overmold step involves injecting the overmold material into a mold cavity that surrounds most or all of the preform sandwich, rather than overmolding to the only the edges of the preforms.

It is preferred that the material added in the overmold step is similar to that utilized in molding the preforms 202; however, in other embodiments the preform material and the overmold material may comprise different but nonetheless suitable materials for manufacturing the seal, as discussed above. Therefore as used herein "a flexible material" refers to any material selected from the class of suitable seal materials as disclosed.

Figure 19D:
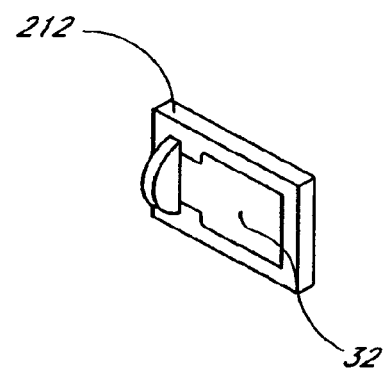
Figure 19E:
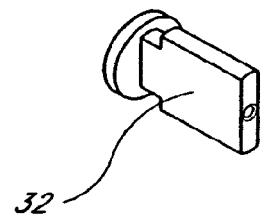
Figure 20:
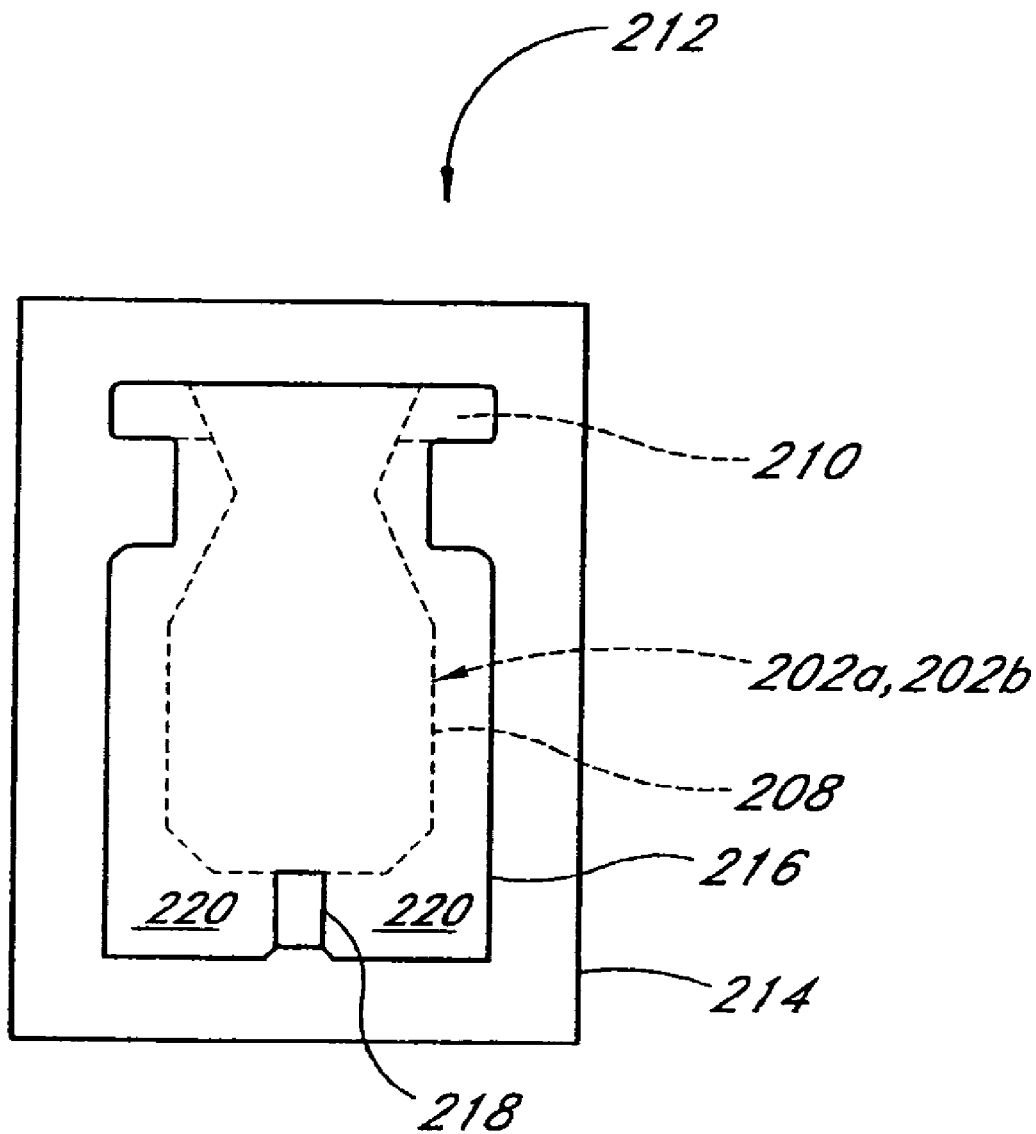
FIG. 20 is a plan view of an overmold plate used in making the seal.

After the overmolding is complete, the mold halves 204a, 206a are removed from the seal plate 212, which now contains a substantially completed seal 32, as seen in FIGS. 19D-19E. The completed seal 32 is easily removed from the seal plate 212, and the seal thus formed comprises, as discussed above, a unitary mass of molded material with the slit arranged within it.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A needleless medical connector having a downstream end for receiving a first medical device and an upstream end for receiving a second medical device, the medical connector comprising:

a housing having an interface configured to receive a connector portion of the first medical device and an axial opening opposite the interface, the housing comprising an upstream end, a downstream end, a cavity extending from the upstream end of the housing to a lower inner surface of the housing, a side inner surface disposed near the upstream end of the housing and defining an offset portion, and a lead cannula extending from the lower inner surface toward the upstream end of the housing; and a seal element having a downstream end in fluid communication with the interface, an upstream end suitable for receiving the second medical device, and a normally substantially closed passage, the seal element comprising a body made of flexible material and having a downstream end and an upstream end opposite the downstream end, a lead lumen formed in the downstream end of the body and in fluid communication with the passage such that in an undisturbed state the lead cannula extends at least partially into the lead lumen, a neck formed proximal to the upstream end of the body, and a transverse flange proximal to an end of the neck opposite the body and having a lower surface, wherein the transverse flange includes a portion disposed upstream of the axial opening and extending radially beyond the side inner surface of the housing, and wherein the body has first and second lateral portions each having an upper surface;

wherein a lower surface of the offset portion of the housing is sufficiently remote from an upper surface of an edge of the axial opening to impart a tensile force to the seal element between the lower surface of the transverse flange and the upper surfaces of the lateral portions, thereby causing a portion of the lower surface of the transverse flange to bear against a portion of the upper surface of the edge of the axial opening and the transverse flange to take on a concave configuration.

2. The medical connector of claim 1, wherein the lead lumen of the seal element is permitted to slide along an outer surface of the lead cannula and to move toward the lower inner surface of the housing when the second medical device is inserted into the medical connector.

3. The medical connector of claim 1, wherein a first distance is defined by the distance between the upper surface of the edge of the axial opening and the lower surface of the offset portion and a second distance is defined by the distance between the lower surface of the transverse flange and the upper surfaces of the lateral portions, the first distance being greater than the second distance.

4. The medical connector of claim 1, wherein the concave configuration biases the opening of the transverse flange towards a closed position.

5. The medical connector of claim 1, wherein the opening in the transverse flange is disposed near the deepest portion of the concavity of the transverse flange.

6. The medical connector of claim 1, wherein the lead cannula is centered on an axis substantially parallel to or collinear with a longitudinal axis of the housing.

7. The medical connector of claim 1, wherein the lead cannula is substantially rigid.

8. The medical connector of claim 1, wherein the housing comprises at least one side opening.

9. The medical connector of claim 1, wherein the housing comprises a seal holder containing the seal element such that the interface is configured to be mateably coupled to the seal holder.

10. The medical connector of claim 1, wherein the medical connector is configured to selectively permit a substantially unobstructed, smooth flow of fluid therethrough.

11. The medical connector of claim 1, wherein upon removal of the second medical device from the seal element, substantially all fluid in the seal element is urged towards the downstream end of the seal element.

* * * * *

UNITED STATES PATENT AND TRADEMARK OFFICE
CERTIFICATE OF CORRECTION

PATENT NO. : 8,221,391 B2
APPLICATION NO. : 12/844791
DATED : July 17, 2012
INVENTOR(S) : Thomas F. Fangrow, Jr.

It is certified that error appears in the above-identified patent and that said Letters Patent is hereby corrected as shown below:

In the Specifications:

At Column 3, Lines 4-6, please move the paragraph appearing at lines 4 through 6 to appear as a continuation of the preceding paragraph at Column 3, Line 3.

In Column 4, Line 55, after "FIG. 14" please insert --is--.

In Column 6, Line 11, please insert a --,-- after "0.228"".

In Column 8, Line 22, please change "V." to --$V_{max.}$--.

Signed and Sealed this
Fourteenth Day of May, 2013

Teresa Stanek Rea
*Acting Director of the United States Patent and Trademark Office*